(12) United States Patent
Casscells, III et al.

(10) Patent No.: US 7,603,166 B2
(45) Date of Patent: Oct. 13, 2009

(54) METHOD AND APPARATUS FOR DETECTION OF VULNERABLE ATHEROSCLEROTIC PLAQUE

(75) Inventors: S. Ward Casscells, III, Houston, TX (US); James T. Willerson, Houston, TX (US); Morteza Naghavi, Houston, TX (US); Bujin Guo, Houston, TX (US)

(73) Assignee: Board of Regents University of Texas System, Austin, TX (US)

( * ) Notice: Subject to any disclaimer, the term of this patent is extended or adjusted under 35 U.S.C. 154(b) by 1433 days.

(21) Appl. No.: 10/640,570

(22) Filed: Aug. 12, 2003

(65) Prior Publication Data

US 2004/0111016 A1 Jun. 10, 2004

Related U.S. Application Data

(63) Continuation of application No. 09/188,661, filed on Nov. 9, 1998, now abandoned.

(51) Int. Cl.
*A61B 5/00* (2006.01)
(52) U.S. Cl. .................. 600/473; 600/476; 600/310; 600/342
(58) Field of Classification Search .......... 600/310, 600/311, 317, 322, 342, 473, 476
See application file for complete search history.

(56) References Cited

U.S. PATENT DOCUMENTS 3,273,395 A 9/1966 Schwarz (Continued)

FOREIGN PATENT DOCUMENTS

EP 0392897 4/1990

(Continued)

OTHER PUBLICATIONS

Alam, M.K., et al. *Appl Spectrosc* 52:393-399 (1998).

(Continued)

*Primary Examiner*—Eric F Winakur
(74) *Attorney, Agent, or Firm*—Conley Rose, P.C.

(57) ABSTRACT

Methods for the detection of inflammation associated with vulnerable atherosclerotic plaque to prevent heart attack and stroke are disclosed. The methods are also applicable to detection of infection, cancer, wounds or auto-immune disease in the body. Certain embodiments of the new methods provide a way of predicting the level of vulnerability of an atherosclerotic plaque to rupture or thrombus formation by assessing via fiber optic NIR spectrophotometry the status of two or more parameters associated with inflamed atherosclerotic plaque in a vessel of a living patient. From these measurements such conditions as low pH, hypoxia, low glucose, oxidative stress or compounds abundant in vulnerable plaque such as oxidized LDL cholesterol and oxidized metabolites of NO, significant active macrophage population, thin plaque cap, as well as senescence and/or apoptosis of smooth muscle or endothelial cells are determined with the assistance of a suitably programmed microprocessor. By considering together the status of some or all of these conditions with respect to successive sites along a vessel wall, particular plaques which are at significant risk of rupturing or thrombosing can be distinguished from "normal" vessel wall and from "intermediate" and relatively stable or "lower risk" plaques. Sites having more of the indicator conditions would be considered most in need of prompt intervention, and certain combinations of parameter levels would be suggestive of relatively stable plaque.

Also disclosed is a multi-parameter catheter and analytical processing assembly for use in the methods.

30 Claims, 10 Drawing Sheets

U.S. PATENT DOCUMENTS

| | | | |
|---|---|---|---|
| 3,638,640 | A | 2/1972 | Shaw |
| 3,866,599 | A | 2/1975 | Johnson |
| 3,913,568 | A | 10/1975 | Carpenter |
| 4,005,605 | A | 2/1977 | Michael |
| 4,200,110 | A | 4/1980 | Peterson et al. |
| 4,281,645 | A | 8/1981 | Jöbsis |
| RE32,204 | E | 7/1986 | Halvorsen |
| 4,602,642 | A | 7/1986 | O'Hara et al. |
| 4,699,147 | A | 10/1987 | Chilson et al. |
| 4,752,141 | A | 6/1988 | Sun et al. |
| 4,776,334 | A | 10/1988 | Prionas |
| 4,777,955 | A | 10/1988 | Brayton et al. |
| 4,784,149 | A | 11/1988 | Berman et al. |
| 4,790,324 | A | 12/1988 | O'Hara et al. |
| 4,794,931 | A | 1/1989 | Yock |
| 4,797,840 | A | 1/1989 | Fraden |
| 4,799,479 | A | 1/1989 | Spears |
| 4,841,981 | A | 6/1989 | Tanabe et al. |
| 4,862,887 | A | 9/1989 | Weber et al. |
| 4,986,671 | A | 1/1991 | Sun et al. |
| 4,995,398 | A | 2/1991 | Turnridge |
| 5,000,185 | A | 3/1991 | Yock |
| 5,046,501 | A | 9/1991 | Crilly |
| 5,057,105 | A | 10/1991 | Malone et al. |
| 5,106,387 | A | 4/1992 | Kittrell et al. |
| 5,109,859 | A | 5/1992 | Jenkins |
| 5,115,137 | A | 5/1992 | Andersson-Engels et al. |
| 5,174,299 | A | 12/1992 | Nelson |
| 5,197,470 | A | 3/1993 | Helfer et al. |
| 5,217,456 | A | 6/1993 | Narciso, Jr. |
| 5,237,996 | A | 8/1993 | Waldman et al. |
| 5,275,594 | A | 1/1994 | Baker et al. |
| 5,279,565 | A | 1/1994 | Klein et al. |
| 5,282,813 | A | 2/1994 | Redha |
| 5,293,872 | A | 3/1994 | Alfano et al. |
| 5,304,173 | A | 4/1994 | Kittrell et al. |
| 5,313,949 | A | 5/1994 | Yock |
| 5,336,178 | A | 8/1994 | Kaplan et al. |
| 5,355,880 | A | 10/1994 | Thomas et al. |
| 5,373,849 | A | 12/1994 | Maloney et al. |
| 5,400,788 | A | 3/1995 | Dias et al. |
| 5,439,000 | A | 8/1995 | Gunderson et al. |
| 5,445,157 | A | 8/1995 | Adachi et al. |
| 5,453,448 | A | 9/1995 | Narciso |
| 5,496,271 | A | 3/1996 | Burton |
| 5,542,915 | A | 8/1996 | Edwards et al. |
| 5,547,472 | A | 8/1996 | Onishi et al. |
| 5,558,093 | A | 9/1996 | Pomeranz |
| 5,582,170 | A | 12/1996 | Soller |
| 5,596,995 | A | 1/1997 | Sherman et al. |
| 5,606,974 | A | 3/1997 | Catellano et al. |
| 5,611,338 | A | 3/1997 | Gallup et al. |
| 5,620,438 | A | 4/1997 | Amplatz et al. |
| 5,623,940 | A | 4/1997 | Daikuzono |
| 5,682,899 | A | 11/1997 | Nashut et al. |
| 5,708,275 | A | 1/1998 | Rhodes et al. |
| 5,733,739 | A | 3/1998 | Zakin et al. |
| 5,792,050 | A | 8/1998 | Alam |
| 5,849,028 | A | 12/1998 | Chen |
| 5,871,449 | A | 2/1999 | Brown |
| 5,924,997 | A | 7/1999 | Campbell |
| 5,935,075 | A | 8/1999 | Casscells et al. |
| 6,816,743 | B2 * | 11/2004 | Moreno et al. ............ 600/473 |

FOREIGN PATENT DOCUMENTS

| | | |
|---|---|---|
| EP | 0856278 | 12/1997 |
| EP | 1025797 | 9/1999 |
| SU | 649410 | 2/1979 |
| WO | 8911311 | 11/1989 |
| WO | 9415529 | 7/1994 |
| WO | 9502362 | 1/1995 |
| WO | 9710748 | 3/1997 |

OTHER PUBLICATIONS

Belli, J. A., et al., "Influence of Temperature on the Radiation Response of Mammalian Cells in Tissue Culture," *Radiation Research*, 18:272-276(1963).

Bellocq et al. *J Biol Chem* 273:5086-5092(1998).

Berliner, J. A., et al., "Atherosclerosis: Basic Mechanisms-Oxidation, Inflammation, and Genetics," *Circulation*, 91(9): 2488-2496, (May 1, 1995).

Biffl, W. L., et al., Interleukin-6 Delays Neutrophil Apoptosis, *Arch Surg.*, 131:24-30 (Jan. 1996).

Blackburn, M.J., et al., "The Sensitivity to Hyperthermia of Human Granulocyte/Macrophage Progenitor Cells (CFU-GM) Derived from Blood or Marrow of Normal Subjects and Patients with Chronic Granulocytic Leukemia," *Br. J. Cancer*, 50:745-751 (1984).

Buja et al., "Role of Inflammation in Coronary Plaque Disruption," *Circulation* 89(1):503-505 (Jan. 1994).

Carney, et al. *Anal Chem* 65:1305-1313 (1993).

Casscells, et al; "Thermal Detection of Cellular Infiltrates in Living Atherosclerotic Plaques; Possible Implications for Plaque Rupture and Thrombosis," *Lancet* 347:1447-49 (1996).

Cassis, et al. *Anal Chem* 65:1247-1256 (1993).

Chen, B. D.M., et al., "Induction of Prostaglandin Production by Hyperthermia in Murine Peritoneal Exudate Macrophages," *Cancer Research* 47:11-15, (Jan. 1, 1987).

DeVries, et al. *FASEB J.* 12:111-118 (1998).

Dempsey, R.J. et al. [lodder@pop.uky.edu], "Near-Infrared Imaging and Spectroscopy in Stroke Research: Lipoprotein Distribution and Disease," [http:Kerouac.pharm.uky.edu/ASRG/Wave/Lipo/lipo.htm].

Dempsey, et al., *Ann N Y Acad Sci* 820:149-169 (1997).

Elkon, D., et al., "Thermal Inactivation Energy of Granulocyte-Monocyte Stem Cells," *Radiation Research*, 87:368-372 (1981).

Ensor, J.E., et al., "Warming Macrophages to Febrile Range Destabilizes Tumor Necrosis Factor-α mRNA Without Inducing Heat Shock," *Am. J. Physiol.* 269:C140-C1146 (1995).

Falk, et al., "Coronary Plaque Disruption," *Circulation*, 92(3):657-671 (Aug. 1, 1995).

Field, S.B., et al., "The Relationship Between Heating Time and Temperature: Its Relevance to Clinical Hyperthermia," *Radiotherapy and Oncology*, 1:179-186 (1983).

Fouqueray, B., et al., "Heat Shock Prevents Lipopolysaccharide-Induced Tumor Necrosis Factor-α Synthesis by Rate Mononuclear Phagocytes," *Eur. J. Immunol.* 1992,22:2983-2987.

Gerweck, LeoE., et al., "Influence of Nutrient on Energy Deprivaiton on Cellular Response to Single and Fractionated Heat Treatments," *Radiation Research* 99:573-581 (1984).

Gronholdt, et al. *Eur Heart J* 19 Supp C:C24-C29 (1998).

Hamilton, Raymond F., et al., "Blemycin Induces Apoptosis in Human Alveolar Macropghages," *Am. J. Physiol.* 269: L318-325 (1995).

Haveman, J. et al. "The Role of Energy in Hyperthermia-Induced Mammalian Cell Inacitvation: A Study of the Effects of Glucose Starvation and An Uncoupler of Oxidative Phosphorylation," *J. of Cellular Physiol.*, 107:234-241 (1981).

Kim, Young-Myeong, et al., "Nitric Oxide Protects Cultured Ray Hepatocytes from Tumor Nectrosis Factor-α Induced Apoptosis by Inducing Heat Shock Protein 70" *Expression*, 272 (2): 1402-1411 (Jan. 10, 1997).

Kobayashi, Eiji, et al., "Cell Cycle-Dependent Heat Sensitization of Murine Granulocyte-Macrophage Progenitor Cells in Regenerating Marrow," *Cancer Research*, 45:1459-1463 (Apr. 1985).

Kunkel, S.L., et al., "Regulation of Macrophage Tumor Necrosis Factor Prodution by Prostaglandin $E_2$," *Biochemical and Biophysical Research Communication*, 137(1):404-410 (May 29, 1986).

Lippman *Exp Geron* 20:1-5 (1985).

Liu. *Biochem Biophys Acta* 1315:73-77 (1996).

Lodder, R. A. et al. [lodder@pop.uky.edu] "Near Infrared Spectrometric Imaging in Stroke Research," [http://Kerouac.pharm.uky.edu/ASRG/PittCon/RAL1995/ROBPIT].

Mangan, Dennis F., "Lipopolysaccharide, Tumor Nectrosis Factor-α, and IL-β Prevent Programmed Cell Death (Apoptosis) in Human Peripheral Blood Monocytes," *The Journal of Immunology*, 146(5):1541-1546 (Mar. 1, 1991).

McShane, et al. *Appl Spectrosc* 52:1073-1078 (1998).

Morange, M., et al., "Interferon Pretreatment Lowers the Threshold for Maximal Heat-Shock Response in Mouse Cells," *Journal of Cellular Physiology*, 127:417-422 (1986).

Muller, et al., "Triggers, Acute Risk +Factors and Vulnerable Plaques: the Lexicon of a New Frontier," *JACC* 23(3):809-813 (Mar. 1, 1994).

Nagata, Shigekazu et al., "The Fas Death Factor," *Science* 267:1449-1456 (Mar. 10, 1995).

Nishina, Hiroshi, et al., "Stress-Signalling Kinase Sek 1 Protects Thymoctyes from Apoptosis Mediated by CD95 and CD3," *Nature* 385:350-353 (Jan. 23, 1997).

Ohdan et al. *Transplantation* 60:531-+535 (1995).

Ohdan et al. *Transplantation* 57:1654-1677 (1994).

Papadimitriou, J.M., et al., "Quantitative Investigations of Apoptosis of Murine Mononuclear Phagocytes During Miled Hyperthermia," *Experimental and Molecular Pathology* 59:1-12 (1993).

Patterson, et al. *FEBS Lett* 434:317-321 (1998).

Pizurki, Lara, et al., "CAMP Modulates Stress Protein Synthesis in Human Monocytes, Macrophages," *Journal of CellularPhysiology*, 161:169-177 (1994).

Prins, Jonannes B., et al., "Apoptosis of Human Adipocytes in Vitro," *Biochemical and Biophysical Research Communications*, 201(2):500-507 (1994).

Reddy, M.V., et al., "Heat Shock Treatment of Macrophages Causes Increased Release of Superoxide Anion," *Infection onad Immunity*, 60(6)L2386-2390 (1992).

Ribeiro, Sergio P., et al., "Effects of the Stress Response in Septic Rats and LPS-Stimulated Alveolar Macrophages: Evidence fro TNF-α Posttranslational Regulation," *Am. J Respir Crit Car Med*, 154:1843-1850 (1996).

Robinson, M.R., et al. *Clin Chem* 38:1618-1622 (1992).

Sivo, Judit, et al., "Heat Shock Mimics Glucocorticoid Effect on IFN-γ-Induced Fc-γRI and Ia Messenger RNA Expression in Mouse Peritoneal Macrophages," *Journal of Immunology*, pp. 3450-3454 (1996).

Snyder, Yvonne M., et al., Transcriptional Inhibition of Endotozin-Induced Monokine Synthesis Following Heat Shock in Murine Peritoneal Macrophages, *Journal of Leukocyte Biology*, 51:181-187 (1992).

Thompson, Craig B., "Apoptosis in the Pathogenesis and Treatment of Disease," *Science*, 267:1456-1462 (Mar. 10, 1995).

Van der Wal, et al., "Site of Intimal Rupture of Erosion of Thrombosed Coronary Atherosclerotic Plaques: Is Characterized by An Inflammatory Process Irrespective of the Dominant Plaque," *Morphology*, 89(1):36-44 (Jan. 1994).

Vaux, D.L., et al., "The Molecular Biology of Apoptosis," *Proc. Natl. Acad. Science USA*, 93:2239-2244 (Mar. 1996).

Verheji, Marcel, et al., "Requirement for Cereamide-Initiated SAPK/JNK Signaling in Stress-Induced Apoptosis," *Nature*, 308:75-79 (Mar. 1996).

Wang, Jiang Huai, et al., "Induction of heat Sock Protein 72 Prevents Neutrophil-Mediated Human Endothelial Cell Necrosis," *Arch Surg.*, 130:1260-1265 (Dec. 1995).

Wang, Jian Huai, et al., "Induction of Human Endothelial Cell Apoptosis Requires Both Heath Shock and Oxidative Stress Responses," *Am. J. Physiol.*, 272:C1543-C1551 (1997).

Westra, Arthur, et al., "Variation in Sensitivity to Heat Shock During the Cell-Cycle of Chinese Hamster Cells in Vitro," *Int. J. Radiat. Biol.* 19(5):467-477 (1971).

Wike-Holley, JL., et al., "The Relevance of Tumour pH to the Treatmetn of Malignant Disease," *Radiotherapy and Oncology*, 2:343-366 (1984).

Zhang, S., et al., *App Spectrosc* 52:400-406 (1996).

\* cited by examiner

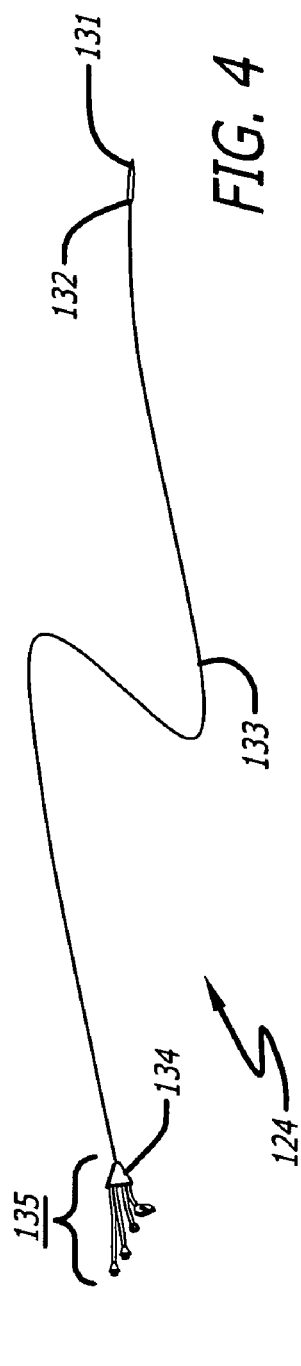
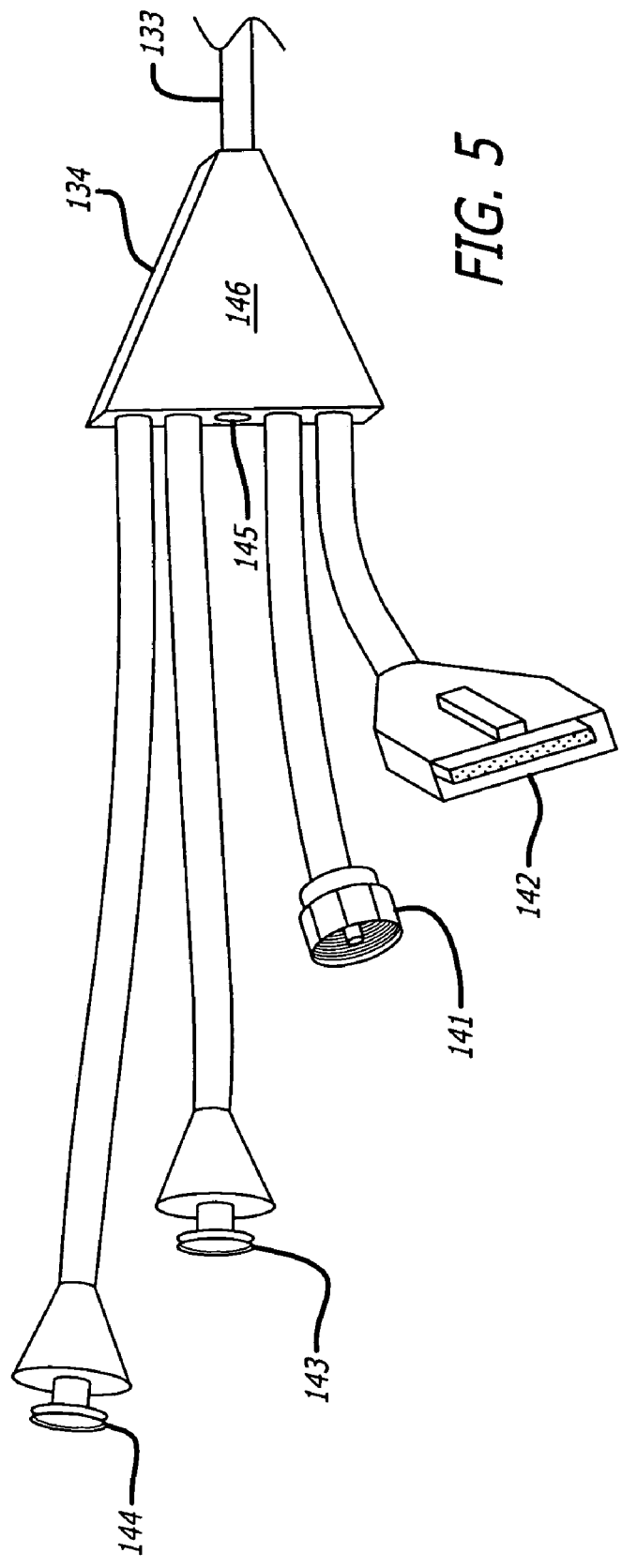
FIG. 4
FIG. 5

METHOD AND APPARATUS FOR DETECTION OF VULNERABLE ATHEROSCLEROTIC PLAQUE

CROSS REFERENCE TO A RELATED APPLICATION

The present application is a continuation application of patent application Ser. No. 09/188,661, filed Nov. 9, 1998, and entitled "METHOD AND APPARATUS FOR DETECTION OF VULNERABLE ATHEROSCLEROTIC PLAQUE".

STATEMENT REGARDING FEDERALLY SPONSORED RESEARCH OR DEVELOPMENT

This invention was made with government support under contact number DAMD17-98-18002 awarded by the United States Army. The government has certain rights in the invention.

BACKGROUND OF THE INVENTION

1. Field of the Invention

The present invention generally relates to methods of diagnosing and treating inflammation, particularly inflamed atherosclerotic plaque at risk of rupture or thrombosis. More particularly, the methods of the invention pertain to the simultaneous detection of two or more chemical parameters associated with inflammation and/or active cellular metabolism in plaque. The invention also relates to multi-parameter catheter assemblies for irradiating sites along a blood vessel wall with near-infrared and visible wavelength radiation and for receiving and analyzing the reflected radiation to qualitatively or quantitatively determine the status of each such parameter.

2. Description of the Related Art

Atherosclerotic coronary artery disease is the leading cause of death in industrialized countries. Typically, patients who have died of coronary disease may exhibit as many as several dozen atherosclerotic plaques in the arterial tree. Plaque, a thickening in the arterial vessel wall, results from the accumulation of cholesterol, proliferation of smooth muscle cells, secretion of a collagenous extracellular matrix by the cells, and accumulation of inflammatory cells and, eventually, hemorrhage, thrombosis and calcification.

Narrowing of the arteries feeding an organ, such as the heart, decreases the flow of blood supplying oxygen and necessary energy substrates to the active cells of the organ. This defect is more pronounced once the organ increases its metabolic activity: this demands an even greater supply which cannot be satisfied due to the inappropriate perfusion resulting from the narrowing. Myocardial ischemia (insufficiency of blood perfusion) is the clinical sign of atherosclerosis characterized by chest discomfort (angina). Over the past decades, several clinical and laboratory tools (such as exercise tests, angiography, and perfusion scans) and therapeutic methods (such as angioplasty, coronary bypass surgery, and atherectomy) have been developed in order to diagnose and treat atherosclerotic disease. These methods are based on the concepts of detecting and treating lumen stenosis (significant narrowing).

Various fiber optic therapeutic catheters have been developed some of which, including the "smart laser" types, attempt to distinguish healthy tissue from atheromatous plaque. For example, U.S. Pat. No. 5,106,387, issued to Kittrell et al., describes such a device. However, the "smart laser" catheter was disappointing in clinical trials (M. B. Leon, M. D., personal communication), and never became an accepted therapy.

Helfer et al. discloses in U.S. Pat. No. 5,197,470 another method of discriminating healthy tissue from diseased tissue in a blood vessel based on characteristic near-infrared reflectance wavelengths attributable to "diseased" or "healthy" conditions. For the purpose of evaluating blood vessel tissue, "diseased" (i.e., plaque) or "healthy" status was determined in those studies by a skilled pathologist who examined each specimen for the presence of cholesterol esters and calcification as the primary distinguishing features. These investigators noted the difficulty of defining and quantifying what is a "diseased state" of the tissue for obtaining meaningful comparative numbers. As with most known methods and devices directed at identifying plaque in a living vessel, this method relies only on anatomo-pathological (histo-pathological) aspects of the plaque. Such features as calcification and cholesterol content are now considered to be poor indicators of the truly dangerous plaques, as discussed very recently in an American Heart Association Monograph entitled "The Vulnerable Atherosclerotic Plaque," Valentine Fuster, M.D., Ph.D., ed., Futura Publishing Co., Armonk, N.Y. (1998).

Vulnerable Plaque

It is now becoming widely recognized that in most instances of myocardial infarction, cardiac arrest, and perhaps stroke, it is only one of an artery's many lesions (plaques) which has actually ruptured, fissured, or ulcerated. The rupture, fissure, or ulcer causes a large thrombus (blood clot) to form on the inside of the artery. Such a large blood clot may completely occlude the flow of blood through the artery, often causing injury to the heart or brain.

It is known that approximately one-half of the unstable coronary atherosclerotic plaques are in arteries with 50% or less luminal diameter narrowing. See, for example, Fuster, V., et al., *N. Engl. J. Med.* 326:242-250 (1992); Fuster, V., et al. *N. Engl. J Med.* 326:310-318 (1992). These are lesions that are hydronomically insignificant, as they cause no resistance to flow and can not be detected by any stress test. Thus, it is very important that a technique be developed which is able to detect the unstable atherosclerotic plaque, independent of the degree of luminal diameter narrowing, and treat it before unstable angina and/or acute myocardial infarction and its consequences occur. A major diagnostic and prognostic dilemma for the cardiologist is how to predict which plaque is about to rupture.

These culprit lesions, referred to as "vulnerable," "dangerous," "unstable" or "at-risk" plaques, have some unique histopathologic features. These features include: a lipid core containing substantial free and esterified cholesterol, and other necrotic debris; infiltrated macrophages (and less frequently lymphocytes, monocytes and mast cells); less abundant smooth muscle cells; and, consequentially, low content of collagen and other matrix proteins. The lipid core, which is mainly a large pool of cholesterol, characterizing most ruptured plaque, results from insudation and from the release of the contents of foam cells following degradation of the cell wall. The low content of collagen and matrix proteins associated with at-risk plaque contributes to an important feature of the unstable plaque—the thin plaque cap. The release of matrix-digesting enzymes by the inflammatory cells is thought to contribute to plaque rupture. Small blood clots, particularly microthrombi, are also frequently found on non-ruptured but inflamed ulcerated plaque surfaces.

This picture of at-risk plaque represents a significant departure from the conventional approaches which assumed the most severely stenosed areas to be the most dangerous areas in an artery. Current thought suggests that vulnerable plaques are actually less likely to be calcified than the more stable plaques. Extensive calcification of the arterial bed has been shown to be closely associated with coronary heart disease (CHD) events, and therefore most likely reflects a vessel's overall atherosclerotic burden rather than localized at-risk lesions. Most cardiovascular specialists currently believe that calcification of a specific lesion does not itself increase the likelihood of rupture of that lesion but instead appears to provide a stabilizing effect.

In recent years the efforts of many investigators have been directed beyond merely distinguishing plaque from healthy vessel wall and aimed toward discriminating the unstable plaques from the more stable ones. For example, others have investigated the lipid and calcium content of plaques using Raman spectroscopy as an indicator of at-risk plaque (Salenius et al. *J Vasc Surg* 27:710-9 (1998); Brennan et al. *Circulation* 96:99-105 (1997); Manoharan et al. *J Photochem Photobiol B* 16:211-33 (1992); and Baraga et al. *Proc Natl Acad Sci USA* 89:3473-7 (1992). U.S. Pat. No. 5,453,448 (issued to Narcisco) describes a spectroscopic fluorescence method for estimating the lipid content of a plaque as an indicator of a potentially dangerous lesion.

Some investigations have identified oxidized low-density lipoproteins (LDL) in plaque based on their NIR spectral signatures (Cassis et al. *Anal Chem* 65:1247-56 (1993); Carney et al. *Anal Chem* 65:1305-13 (1993); and Dempsey et al. *Ann N Y Acad Sci* 820:149-69 (1997)). Detection methods based on locating lipid or fat pools associated with unstable plaques are based on the fact that fat is very thrombogenic and is most likely to be found in total coronary occlusions which have occurred following a plaque rupture. It is well known that the lipid content of arterial wall is found to a great extent in benign fatty streaks along the walls rather than only at neointimal sites of proliferated smooth muscle cells and macrophages. Lipid that has insulated (e.g. filtered into and bound to the arterial wall), as occurs from the early years of life, is not by itself considered to be a dangerous lesion. Typically, fatty-streaked vessels are scattered throughout the arterial tree, but less so in internal brachial and radial arteries. Many times, a benign fatty lesion is located exactly adjacent to a vulnerable plaque. Therefore, probing for lipid pools or even oxidized LDL would not be expected to provide an adequate way of diagnosing unstable plaque.

A recent study aimed at characterizing vulnerable plaques by NIR spectroscopy in the atherosclerotic rabbit model is described by Moreno, et al. (*Circulation* 17:1-1016 (1998 Suppl). This study correlated NIR spectra with the histological features of thin fibrous cap, lipid pool, macrophages and calcium content.

Each of these methods fails to recognize the functional activity level of atherosclerotic plaque however. They do not focus on chemical factors indicative of activated macrophages, and fail to provide an adequate way to identify the truly dangerous plaques at risk of rupturing or thrombosing. Methods relying on detection of calcium in vulnerable plaque are particularly problematic in view of the now widely-held view that calcified plaques are actually less likely to be vulnerable to rupture since the calcium deposit of the plaque can provide a type of physically supportive skeleton.

Inflammation

Inflammation can typically be found at sites in the body where there is infection, cancer, a wound or auto-immune disease activity. There is also a great deal of evidence showing that atherosclerosis exhibits an active process of inflammation. Inflammation in an arterial plaque is also believed to be the result of a series of biochemical and mechanical changes in the arterial wall (See, e.g., Gronholdt et al. *Eur Heart J* 19 Supp C:C24-C29 (1998)). Both chemical inflammatory mediators (like cytokines) and cellular and humoral components of inflammation have been described as taking part in the atherosclerosis chronic process—from the very first steps of endothelial injury to the late stages of rupture and also restenosis. The late events of atherogenesis are believed to be due to an exacerbation of the chronic inflammatory process.

Of the several elements of inflammation in plaque, macrophages and cytokines seem to be most crucial with respect to the phenomenon of plaque rupture. Inflamed plaque is believed to behave as an active, but not necessarily acute, site of inflammation in the body. (See, e.g., Berliner et al. *Circulation* 91:2488-96 (1995); DeGraba, T J *Neurology* 49:S15-9 (1997); Tenaglia et al. *Am J Cardiol* 79:742-7 (1997); Watanabe et al. *Int J Cardiol* 54 Suppl:S51-60 (1997); Kristensen et al. *Am J Cardiol* 80:5E-9E (1997); van der Wal et al. *Coron Artery Dis* 5:463-9 (1994); Vos et al. *Virchows Arch B Cell Pathol Incl Mol Pathol* 43:1-16 (1983); Schroeder et al. *Atherosclerosis* 118 Suppl:S141-9 (1995); Libby et al. *J Cardiovasc Pharmacol* 25 Suppl 2:S9-12 (1995); Bjorkerud et al. *Am J Pathol* 149:367-80 (1996) [see the comments in Bjorkerud, in particular]; Willerson J T *Adv Intern Med* 43:175-202 (1998); Boyle J J *Pathol* 181:93-9 (1997)).

As described in U.S. patent application Ser. No. 08/717, 449 (Casscells et al;) and in *Lancet* 347:1447-1449 (1996), sites of inflamed atherosclerotic plaque typically exhibit elevated temperature over adjacent ambient vessel wall temperatures. Human carotid endarterectomy specimens display temperature heterogeneity ranging from 0.2°-4° C. The highest temperatures are found at sites of macrophage and T-cell infiltration in or beneath thin fibrous caps. This increased temperature is thought to be due primarily to increased metabolic activity, oxygenation and vasodilation at the site. The atherosclerotic plaque with elevated temperature has the morphological characteristics of those plaques likely to ulcerate, leading to thrombosis (see for example Falk, E., et al. *Circulation* 92:657-71 (1995); Davies, M J *Lancet* 347:1422-3 (1996); Falk, E. *Am. J. Cardiol.* 63:114E-120E (1989); Fuster, V., et al., *Circulation* 82:1147-59 (1990); Davies, M. J., et al. *Brit. Heart J.* 53:363-373 (1985); and Libby, P. *Circulation* 91:2844-2850 (1995)).

Other investigators have shown that individuals with increases in their serum C-reactive protein, fibrinogen, P selectin, and Von Wildebrand factor levels are at increased risk for future thrombotic vascular events (e.g., see Liuzzo, G., et al. *N. Engl. J. Med.* 331:417-424 (1994); Itoh, T., et al. *Coronary Artery Disease* 6:645-650 (1995); Ridker, P. M., et al., *N. Engl. J. Med.* 336:973-979 (1997); Liuzzo, G., et al., *Circulation* 94:2373-2380 (1996); Wu, K. K., *Int. J. Clin. Lab. Res.* 27: 145-152 (1997)). Disruption of fibrous plaque caps often occurs at points of ongoing inflammation, indicated by the presence of activated macrophages (Gronholdt et al., id).

Active inflammation sites, wherever found in the human body, are usually characterized by increased secretion of cytokines and chemotoxic factors, hypermetabolic status (as indicated by increased ATP consumption, low pH, increased reactive oxygen species (e.g. free radicals), relatively low oxygen and glucose levels, and elevated lactate and other anaerobic metabolites, (depending on the vascularity of the site). (See, for example, Chavalittamrong et al. *Respiration* 38:112-20 (1979); Davies et al. *Agents Actions* 6:60-74 (1976); Strukov, A I *Arkh Patol* (Russian) 45:73-6 (1983).) Some of these chemical or biochemical analytes have been characterized in certain clinical and physiological situations such as brain oxygenation studies and myocardial oxygenation during ischemia-reperfusion, and NIR spectroscopy has been employed for their detection. However, these techniques have not typically been used for monitoring inflammation. Moreover, none of them have been utilized for diagnosing atherosclerotic plaque in a living vessel.

pH

Tissue pH is an important physiological parameter that can indicate both blood flow and the metabolic state of a cell. Generally, cell activation leads to acidification of extracellular pH due to excretion of acidic metabolites such as lactate and $CO_2$. These changes are associated with activation of the cells by various signal transduction pathways. As pointed out above, disruption of plaque caps often occurs at points of active inflammation, indicated by the presence of activated macrophages (van der Wal, et al. *Circulation* 89:36-44 (1994)). De Vries et al. (*FASEB J* 12:111-118 (1998)) monitored in vitro the direct effects of oxidized LDL on the cellular metabolism of macrophages, as evidenced by changes in the extracellular pH. Patterson et al. (*FEBS Lett* 434:317-321 (1998)) noted that atherosclerotic lesions may have an acidic extracellular pH as low as 3.6.

Twining et al. (*Curr. Eye Res.* (1984) 8:1055-62) have shown in rabbits that during macrophage invasion vitrial pH was reduced from 7.4 to 6.2. NIR spectroscopic measurements and the partial least squares (PLS) multivariate calibration technique were combined to monitor the deep tissue pH values. The PLS loading factors show that the spectral features related to pH changes are due to several components in the tissue, including but not limited to hemoglobin, myoglobin, and cytochrome aa3.

The hydrogen ion does not exhibit infrared bands. However, hydrogen ions will bind to other species in solution that are infrared active, thus a correlation for pH can be based on secondary spectroscopic effects. Zhang, S. et al. (*App Spectrosc* (1998) 52:400-406 describes a non-invasive method of determining deep-tissue pH based on the NIR spectra of skeletal muscle. Alam, M. K. et al. (*Appl Spectrosc* 52: 393-399 (1998) and U.S. Pat. No. 5,792,050) describes the non-invasive measurement of pH based on the NIR absorption spectrum (in the 1000-2500 nm wavelength range) of the C—H bond of the second and fourth carbon in the heterocycle of histidine in hemoglobin. See also, Soller et al. *J Clin Monit* 12:387-95 (1996). Of the known methods of measuring pH, none has been used for assessing the pH of atherosclerotic plaque as an indicator of level of risk of rupture or thrombosis.

Oxygenation

Ohdan, H. et al. (*Transplantation* 57:1674-1677 (1994); *Transplantation* 60:531-535 (1995)) describe the use of near-infrared spectroscopy to quantify nitric oxide, in conjunction with the measurement of oxyhemoglobin (oxy-Hb) and deoxyhemoglobin (deoxy-Hb) during acute rejection of liver allograft. This was possible due to the different NIR spectra of nitrosyl-hemoglobin (nitrosyl-Hb), oxy-Hb, deoxy-Hb, cytochrome oxidase (oxidized $Cytaa_3$) and reduced cytochrome oxidase (reduced $Cytaa_3$). Mangat et al. J. Mol. Cell. Cardiol. 30:A235 (1998) describes visible and near-infrared monitoring of oxidant effects on myocardial tissue during ischemia-reperfusion in a Langendorff perfused heart. None of the known methods of measuring tissue oxygenation has previously been tested used to examine atherosclerotic plaque.

U.S. Pat. No. 3,638,640 (issued to Shaw) describes the use of three or more wavelengths of light to indicate the oxygen saturation of blood at a measurement site. Cytochrome oxidase $aa_3$ ($Cytaa_3$), the terminal member of the intramitochondrial respiratory chain responsible for cell oxidation, is usually hyperactive in active metabolic conditions, and its redox status may indicate the oxidative stress of the cell. The measurement of cerebral cellular oxygenation (oxidized cytochrome oxidase aa3) via non-invasive near-infrared spectroscopy has been described by Nollert, G., et al. (*Circulation* 92:11-327-333 (1995). U.S. Pat. No. 4,281,645, issued to Jobsis, describes near-infrared spectrophotometric assessment of oxyhemoglobin and of the redox state of cytochrome oxidase $aa_3$. Also, see Cooper et al. *Adv Exp Med Biol* 413: 63-73 (1997); Dobrogowska-Kunicka et al. *Neurol Neurochir Pol* 31:1227-37 (1997); Hoshi et al. *J Appl Physiol* 83:1842-8 (1997); Kang et al. *Biomed Instrum Technol* 31:373-86 (1997; Kohl et al. *Phys Med Biol* 43:1771-82 (1998); Piantadosi et al. *Anal Biochem* 253:277-9 (1997); Steinberg et al. *Adv Exp Med Biol* 428:69-77 (1997); Thorniley et al. *Clin Sci* (*Colch*) 91:51-8 (1996)). None of the known methods of measuring cytochrome aa3 has been applied to assessing the level of oxygenation in plaque.

U.S. Pat. No. 5,611,338, issued to Gallup et al., describes a multi-purpose multi-parameter catheter for simultaneously monitoring cardiac output and intra-arterial oxygen concentration in the blood, employing a thermistor and fiber optics. This multi-parameter catheter is not suitable for measuring plaque oxygenation.

Glucose and lactate have been determined simultaneously using near-infrared spectrometry. McShane et al. (*Appl Spectrosc* 52: 1073-1078 (1998)) have recently described a method of quantitating glucose and lactate in cell culture by non-invasive near-infrared spectroscopy. Berger et al. (*Spectrochim Acta A Mol Biomol Spectrose* 53A:287-92 (1997) describe determination of glucose concentrations in whole blood samples using near-infrared Raman spectroscopy.

The prior art methods and devices fail to provide a clinically useful way of determining which lesion is dangerous and needs pre-emptive treatment. Of the known methods directed at the detection of vulnerable plaque, none is adequate for distinguishing macrophage infiltrated, inflamed plaque from more stable plaque or normal vessel wall. Moreover, none of the existing methods which attempt to locate the most dangerous plaques takes into account the considerable heterogeneity of macrophages in atherosclerotic plaque. A major shortcoming of the prior methods is that none are capable of determining the presence of specific analytes and physiological variables correlated to macrophage activity. Although near-infrared (NIR) spectroscopy has been employed to measure certain chemical factors, there is at the present time no method for studying analytes associated with vulnerable, rupture-prone atherosclerotic plaque. What is needed is a method and device with the ability to cooperatively or simultaneously detect and measure localized functional expression, or activity, or status of the above-mentioned parameters inside a vessel or organ in the body. Such measurements would provide an indication of the extent of active inflammation and/or of the presence of a population of actively metabolizing cells at a particular site. A single device efficiently combining means for detecting these parameters, especially in combination, would provide substantial advantages for increasing the specificity and accuracy of diagnostic tools for early detection of dangerous atherosclerotic plaques. Cardiologists, in particular, could use a method and catheter assembly combining detection of such various tissue conditions as hypoxia, low pH, oxidized collagen, elevated or depressed levels of nitric oxide metabolites, elevated lactate, lowered glucose level, presence of oxidized species, and the like, to gain more insight into a plaque's inflammatory status, and as part of interventional diagnostic and treatment procedures requiring probing of inflammatory plaque. With such a multi-parameter catheter and method, and by weighing the information obtained as to a plaque's inflammatory status and physical appearance, it will be possible to more accurately predict and prevent specific plaque rupture.

SUMMARY OF THE INVENTION

The methods and devices of the present invention provide an improvement over known methods and devices for distinguishing vulnerable plaque in a living vessel. As used herein, the term "at-risk", "vulnerable," "dangerous" or "unstable" plaque means an atherosclerotic plaque which, in a living vessel, is likely to develop a fissure, rupture or develop a thrombus leading to a life-threatening event. While most prior art methods are aimed at detecting and treating lumen stenosis, the present invention provides detection of an earlier stage of disease that precedes hemodynamically significant narrowing of the artery. This is an important advantage, especially since research over the past decade has established that these lesions account for most fatal myocardial infarctions (heart attacks) and many strokes. The methods and apparatus of the present invention provide for the first time a clinically useful tool to determine which lesion is dangerous and needs pre-emptive treatment.

One feature of the new methods is the ability to measure particular analytes and physiological variables specifically correlated to macrophage activity in atherosclerotic plaque. Preferred methods of the invention advantageously employ a new visible-near infrared catheter assembly, or use non-invasive detection methods to find and/or to follow dangerous plaques by probing the same macrophage activity markers.

A primary object of the present invention is to provide a way to more specifically identify vulnerable (at-risk) plaque in a living patient by assessing the status of two or more chemical or biochemical parameters associated with vulnerable plaque. Another object of the invention is to provide a method of predicting a level of risk of an atherosclerotic plaque by detecting, measuring, or quantifying two or more parameters associated with plaque that is at risk of rupture or thrombus formation. Another object of the invention is to provide a method of identifying at-risk plaque by examining a vessel or body cavity wall using the new multi-parameter catheter apparatus. Another object is to provide a method of distinguishing dangerous plaque from vessel wall tissue and from relatively stable plaque. It is also an object of the present invention to provide a method of detecting inflammation due to infection, cancer or auto-immune disease, or due to a clinically silent wound.

Another object of the invention is to provide a multi-parameter catheter apparatus for detecting at-risk atherosclerotic plaque based on visual and/or near-infrared spectral analysis of successive sites along a vessel wall. Still another object of the invention is to provide a multi-parameter catheter/detector/processor assembly for use as an investigative tool to identify at-risk plaque by obtaining near-infrared spectral data for two or more parameters at successive sites along a vessel wall. Still another object of the invention is to provide an analytical system for establishing standard infrared or near-infrared spectra for parameters associated with at-risk plaque, and for receiving, processing and analyzing visual images and/or near-infrared spectra obtained from a multi-parameter catheter, whereby a predictive level of risk for plaques can be determined.

In accordance with the present invention, a method of detecting a vulnerable atherosclerotic plaque on a vessel wall is provided. The method includes simultaneously measuring in a site on a living vessel wall two or more chemical parameters associated with actively metabolizing cells (such as macrophages and other inflammatory cells, and smooth muscle cells). It is these highly active cells which are present in inflamed vulnerable atherosclerotic plaque. The qualitative or quantitative measurement of at least two of the following parameters is performed: pH, nitrosyl hemoglobin, nitrosyl tyrosine, glucose, lactate, oxidized collagen, oxyhemoglobin, reduced hemoglobin, oxidized cytochrome oxidase $aa_3$. A preferred embodiment measures pH and oxidized collagen and, optionally, at least one other parameter from the following group: nitrosyl hemoglobin, nitrosyl tyrosine, glucose, lactate, oxyhemoglobin, deoxyhemoglobin and oxidized cytochrome oxidase $aa_3$. In certain embodiments, the method also includes detecting leakage of dye into a plaque whereby a plaque cap fissure is revealed. The detection is accomplished by simultaneously measuring in a living vessel at least two chemical parameters, factors, or analytes, associated with inflamed vulnerable atherosclerotic plaque. This includes providing a fiber optic catheter having an illumination fiber bundle and a detection fiber bundle capable of, respectively, directing light onto or receiving light from a site on a vessel wall, the catheter having means for reducing optical interference by blood or other fluid within a vessel when undergoing examination. It also includes providing a source of 400-2500 nm wavelength light and a spectrometer, each operatively linked to the corresponding fiber bundle.

The invention also provides a processor operatively linked to the spectrometer containing algorithms and reference measurements for at least two chemical parameters associated with actively metabolizing cells in inflamed vulnerable atherosclerotic plaque. The spectrometer and processor are cooperatively linked so that they are capable of receiving and analyzing spectral data collected by the detection fiber bundle and report parameter measurements that correspond to the spectral data. Optionally included is a display system, such as a video monitor, for displaying the information from the processor. The measurement procedure includes measuring a desired parameter at multiple sites on a vessel wall, and also measuring at least one other parameter at the same sites. This large number of measurements, corresponding to many sites along the vessel wall, are then analyzed with the aid of a suitably programmed processor to provide a qualitative or quantitative value for each parameter with respect to particular sites or regions on the vessel wall.

In some embodiments, the processor also contains algorithms and reference measurements for the calorimetric measurement of thrombi (blood clots) colored red (rich in fibrin and erythrocytes), brown (or greenish-brown, indicating an old thrombus) and white (platelet rich). In this embodiment the spectrometer and processor together are able to receive and analyze spectral data collected by the detection fiber bundle, and to report the corresponding colorimetric measurements.

In certain embodiments the display system which receives and displays a report from the processor includes a monitor for displaying a color image of both normal and diseased areas of the vessel wall.

In some embodiments the detecting of vulnerable plaque also includes identifying leakage of dye into a plaque whereby a plaque cap fissure is revealed. A preferred method of detecting in a living vessel an atherosclerotic plaque at risk of rupturing or thrombosing includes qualitatively or quantitatively measuring at least two parameters associated with inflamed vulnerable plaque, as described above; measuring dye sequestered beneath the surface of a site along a vessel wall; and analyzing the dye measurement together with the parameter measurements to obtain a predicted level of risk for at least one site or group of sites on the vessel wall. If the dye that is selected containing a 400-2,500 nm wavelength radiation absorbing chromophore, the measuring of dye sequestration may be performed with the fiber optic catheter along with the other chemical parameters. In this case, the processor is additionally programmed with algorithms and reference measurements for analysing reflected or scattered radiation from the dye chromophore. An alternative way of measuring the dye sequestration is by angiography, in which case the dye is radiopaque to x-rays, and the processor or computer is also capable of receiving and analyzing the angiographic data.

Certain preferred methods of detecting a vulnerable atherosclerotic plaque provide for additionally monitoring the visible color image of the vessel wall, and analyzing what is seen in the visual image together with the chemical and dye penetration measurements.

In accordance with the methods of the present invention, a method of distinguishing vulnerable plaque in need of therapeutic intervention from relatively stable plaque or non-diseased tissue in a living vessel wall is provided. Chemical parameters are measured and analyzed as described above, but the analysis also includes comparing the qualitative or quantitative values for a site or group of adjacent sites to similarly obtained values for another site or group of sites along the vessel wall. In this way a qualitative or quantitative value for each of the desired parameters is reported for particular sites or regions along the vessel wall, expressed in terms relative to other sites or groups of sites along the same vessel wall.

Certain embodiments of the methods of the present invention provide a method of predicting the level of risk of an atherosclerotic plaque on a vessel wall. This method includes identifying areas having a pH of less than 7.2 and identifying areas that have an amount of oxidized collagen that is indicative of a thin or weak plaque cap. In this embodiment, areas having red microthrombi are also identified, as well as those areas that have taken up and sequestered an indicator dye beneath the surface of a vessel. Once these parameters have been measured along the vessel wall, the values for at least two areas are then correlated with a particular vessel site, or group of adjacent sites on the vessel wall. From these correlations a predictive level of risk for each said site or group of sites is determined.

A method of treating a patient known to be suffering from atherosclerotic vascular disease and suspected of being at risk of experiencing a plaque rupture and/or an occlusive thrombotic event, is also provided by the present invention. The method comprises detecting an atherosclerotic plaque at risk of rupturing or thrombosing by taking chemical parameter measurements and dye sequestration measurements, as described above, and, optionally but preferably including monitoring the visible color image of the site and analyzing the visual image together with the chemical parameter and dye measurements, to obtain a predictive level of risk. Knowing the predicted level of risk for at least one site or group of sites on a wall of said vessel, at least one vulnerable plaque is then targeted for treatment. A localized therapeutic intervention or treatment is then administered to at least one of the targeted plaques. Suitable treatments can then be administered, for example, balloon angioplasty, laser angioplasty, heated balloon (RF, ultrasound or laser) angioplasty, surgical atherectomy, laser atherectomy, the placement of an appropriate stent, another conventional mechanical or irradiation treatment method, and pharmacological treatment regimens including anti-coagulants, fibrinolytic, thrombolytic, anti-inflammatory, anti-proliferative, immunosuppressant, collagen-inhibiting, endothelial cell growth-promoting, and conventional pharmacologically appropriate local treatments effective for reducing or eliminating inflamed plaque.

Also in accordance with the present invention, a multi-parameter catheter is provided. The catheter comprises distal and proximal ends and a long conduit lies between the two ends. The catheter has an outer wall and an inflatable balloon attached to the outer wall and circumferentially disposed about a portion of the distal end of the catheter. The catheter also has a window in the outer wall of the catheter's distal end, the window being transparent to 400-2,500 nm wavelength radiation. The catheter has an illumination lumen and a detection lumen, each of which extends longitudinally through the catheter and to the window. A guidewire lumen extends longitudinally through the catheter to a terminus on the catheter's distal end. There is a balloon inflation lumen that is open to an aperture in the catheter's outer wall that is inside the region that the balloon encloses. Optionally, a fluid transporting lumen extends longitudinally through the catheter to a fluid outlet in the catheter's distal end. The catheter also includes a fiber optic illumination bundle containing a multiplicity of illumination fibers capable of transmitting approximately 400 to 2500 nm wavelength radiation, and the catheter has a fiber optic detection bundle, containing a multiplicity of detection fibers similar to those of the illumination bundle. The distal ends of each fiber optic bundle form circular arrays of single fibers adjacent the outer wall of the catheter, the array of illumination fibers are situated between the array of detection fibers and the outer wall. So that the radiation emitted from the illumination fibers can focus on particular sites on the vessel wall, and so that radiation received from particular sites on the vessel wall can be focused into particular detection fibers, a focusing device such as a mirror is positioned at the distal ends of the straight fibers. Alternatively, the fiber distal ends are curved or bent toward the vessel wall. A manifold is attached to the conduit at the catheter's proximal end, the manifold having a guidewire aperture and an illumination connector, detection connector, balloon inflation connector and optional perfusion connector branching out from it opposite a conduit attachment point on the manifold.

The present invention also provides a multi-parameter analyzer for diagnosing an atherosclerotic plaque at risk of rupture or thrombosis. The analyzer comprises the catheter described above and a light source operatively linked to the proximal end of each of the illumination fibers. The light source is able to emit radiation of about 400 to 2,500 nm wavelength. The analyzer also includes a spectrometer operatively linked to each of the detection fibers' proximal ends and is able to convert a multiplicity of optical signals arising from various sites along the vessel wall into corresponding digital signals. A processor, or computer, is operatively linked to the spectrometer and contains suitable algorithms and reference data for storing and analyzing a multiplicity of digital signals and determining a qualitative or quantitative value for at least two parameters associated with actively metabolizing cells of inflamed vulnerable atherosclerotic plaque whereby a risk value indicative of the level of risk of rupture or thrombosis is determined. The analyzer also includes a display system operatively linked to the processor and which displays the parameter values and/or risk values. At the option of the user, a microcontroller may also be operationally linked to the light source, spectrometer and/or signal processor. Preferably the new analyzer is programmed to analyze spectral signals arising from at least two of the following chemical parameters: pH, oxyhemoglobin, deoxyhemoglobin, oxidized cytochrome oxidase $aa_3$, reduced cytochrome oxidase $aa_3$, oxidized collagen, glucose, lactate, and metabolites of nitric oxide such as nitrosyl hemoglobin, nitrosyl tyrosine, peroxynitrite and peroxynitrate.

Still further provided by the present invention is a method of detecting atherosclerotic plaque at risk of rupturing or thrombosing which employs the multi-parameter analyzer described above. According to this method, a conventional angioplasty guidewire is inserted into a vessel and the catheter is introduced into a vessel by sliding along the guidewire until the distal end of the catheter is situated at a desired location in the vessel. By advancing or retracting the catheter, as needed, the transparent window is situated adjacent a point on a vessel wall, which may be an atherosclerotic plaque or a non-diseased site on the vessel wall. The balloon is inflated or deflated such that any fluid in the vessel is substantially excluded between said window and said vessel wall, in order to reduce or eliminate interference with the near-infrared and visible wavelength radiation passing between the optic fibers and the sites on the vessel wall. Optionally, means for detecting infrared radiation emitted from a site on the vessel wall is provided. Thermal radiation—or heat—is detected from a site prior to irradiating the site with visible-near-infrared radiation. After suitably positioning the catheter in the vessel at a first position, the illumination source is operated such that the illumination fibers nondestructively irradiate a multiplicity of radially spaced sites with 400-2,500 nm wavelength radiation. Reflected radiation arising from the irradiated sites is received by the array of detection fibers, assisted by a focusing mirror or by bent or curved fiber tips, and transmitted through the detection fibers to the spectrometer. The spectrometer is operated such that 400-2.500 nm wavelength radiation arising from the multiplicity of sites is received and converted to a corresponding multiplicity of digital signals. The signal processor is operated such that the digital signals are received, stored and analyzed. In cooperation with the operation of the signal processor, the catheter is repositioned to a second position, and then to subsequent positions, preferably at predetermined intervals, for example, by motorized pullback while the illumination source continues to operate and additional data is continuously transmitted to and processed by the spectrometer and processor. At the option of the user, additional angiography data may be input by a keyboard or other input device, into the signal processor for analysis together with the digital signals arising from sites along the vessel wall. The processor is programmed with algorithms and calibration data allowing it to analyze spectral signals arising from at least two chemical parameters, which are, preferably: pH, oxyhemoglobin, deoxyhemoglobin, oxidized cytochrome oxidase $aa_3$, reduced cytochrome oxidase $aa_3$, oxidized collagen, glucose, lactate, and metabolites of nitric oxide (such as nitrosyl hemoglobin, nitrosyl tyrosine, peroxynitrite and peroxynitrate), or another analyte associated with actively metabolizing cells in inflamed vulnerable plaque. As a result of the analysis, qualitative or quantitative values for at least two of the chemical parameters is reported by the processor, correlating the parameter values with particular sites or groups of sites along the vessel wall. At the option of the user, a visible image of a site or group of sites on the vessel wall and/or the analysis report is displayed on a monitor attached to the processor.

Still further provided by the present invention is an improved method of detecting vulnerable atherosclerotic plaque in a living vessel in which a chemical or biochemical component of a plaque is measured, or assayed. This improvement over other methods includes measuring analytes that are associated with, or are characteristic of, activated macrophages. Representative analytes which, in combinations of two or more, are good indicators of the activity level of cells in a plaque cells, are: pH, oxyhemoglobin, deoxyhemoglobin, metabolites of nitric oxide such as nitrosyl hemoglobin and nitrosyl tyrosine, oxidized cytochrome $aa_3$, reduced cytochrome $aa_3$, glucose, lactate and oxidized collagen. In certain embodiments, visible and near-infrared spectroscopy is used to measure the analytes. If preferred, magnetic resonance spectroscopic imaging can be used instead of the NIR catheter in order to measure the analytes non-invasively.

The present invention also provides an improved way of differentiating atherosclerotic plaque at risk of rupturing and occluding from plaque not presently at risk, which goes beyond the known methods of analyzing optical radiation from a site along a vessel wall. The new method focuses on identifying sites containing indicia of highly metabolically active cells.

Yet another embodiment of the present invention provides a method of detecting a localized infection, cancer, a wound or autoimmune disease in the body. Inflammation, as a sign of the infection, cancer, wound or autoimmune disease, is biochemically detected by measuring at a site in the body by combination of parameters chosen from the group consisting of pH, oxyhemoglobin, deoxyhemoglobin, cytochrome oxidase $aa_3$, reduced cytochrome oxidase $aa_3$, nitrosyl hemoglobin, nitrosyl tyrosine, glucose and lactate.

The methods and apparatus of the present invention go beyond the existing methods and devices for identifying a site of infection, cancer, a wound or the presence of autoimmune disease, and is particularly advantageous for identifying dangerous, rupture-prone plaque. Testing a vessel wall for combinations of specific chemical analytes associated with vulnerable plaque provides a better approach to distinguishing the particularly at-risk plaques from relatively stable atherosclerotic plaques in a living vessel.

These and other objects, features and advantages of the present invention will become apparent with reference to the following description and drawing.

BRIEF DESCRIPTION OF THE SEVERAL VIEWS OF THE DRAWING

For a detailed description of a preferred embodiment of the invention, reference will now be made to the accompanying drawings wherein:

FIG. 4 is a high-level view of the catheter of FIG. 3.

FIG. 5 is an enlarged view of the catheter connectors of FIG. 4.

Figure 1:
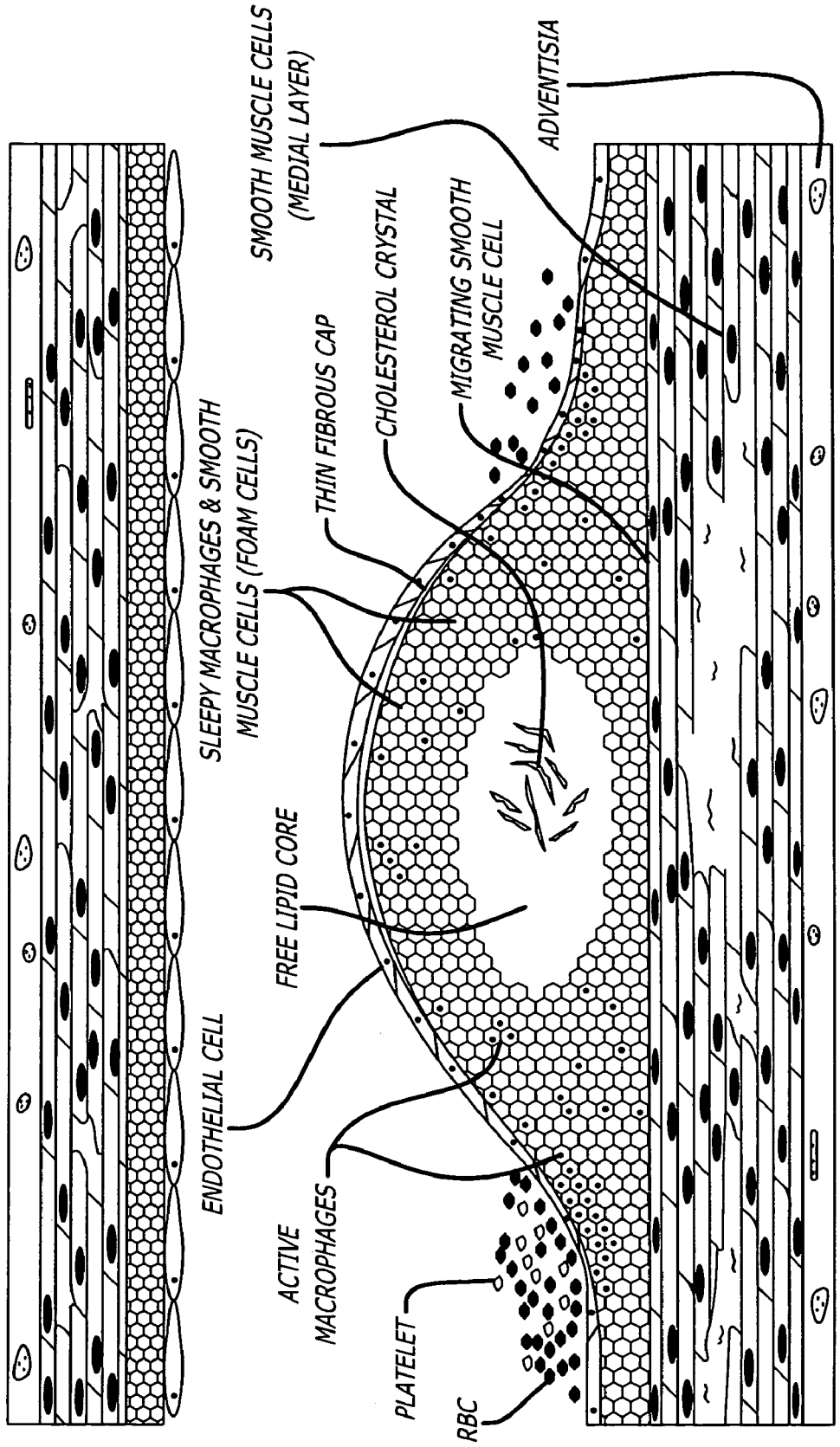
FIG. 1 is a conceptual drawing of an at-risk atherosclerotic plaque in a vessel, shown in longitudinal cross section.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

FIG. 1 depicts an atherosclerotic plaque within a vessel resulting from a chronic, continuous process of lipid infiltration into intima, endothelial injury, leukocyte migration into the subendothelial area, continuous lipid accumulation inside the macrophages, endothelial thickening and, smooth muscle cell proliferation and consequential increased matrix protein and collagen production and a fibrotic cap. In some (usually advanced) cases calcium deposition also occurs, leading to increased mass of the plaque, which causes it to gradually protrude eccentrically towards the endoluminal space and narrow the lumen of the artery. However, when a plaque instead progresses to a vulnerable plaque, as shown in FIG. 1, it is characterized largely by the presence of active macrophages, free lipid core, thin fibrous cap, endothelial denudation and microthrombi. Due to some not yet completely understood mechanism (perhaps hemodynamic parameters), disruption of these plaques usually occurs at its shoulder, especially following a change in blood shear stress. The presence of an extremely thrombogenic lipid core, plus other factors such as tissue factor, causes the rapid acceleration of thrombosis formation following rupture of a plaque. In some cases this thrombosis can quickly occlude the lumen and in still other cases, due to active local fibrinolysis, result in a self-controlled clot formation on the plaque which may reduce the lumen but not completely occlude it. This is believed to be the main underlying pathology of acute coronary syndrome. However, plaque disruption does not always result in an acute event such as a complete coronary occlusion. In fact, depending on the coagulation and thrombolytic balance over the endothelial layer, it quite often may lead to a self-limited injury like a wound with fissure or endothelial erosion and denudation covered by a thin layer of thrombus. Pathologic reports reveal that 15-20% of non-cardiac sudden deaths demonstrate at least one of these patterns (Davies et al. *Eur Heart J* 10:203-8 (1989)). As discussed above in the background of the invention, in these cases where arterial narrowing is not significant, the predictive value of methods based on the old "significant narrowing" concept are of little consequence. It is necessary to both visually and functionally assess the condition of the vessel wall and the plaque itself—rather than merely imaging the lumen—in order to more precisely identify the vulnerable plaques.

The inventors have postulated that inflamed atherosclerotic plaque behaves like an active chronic inflammation site, rather than an acute inflammation site. Sites of chronic inflammation generally comprise fewer inflammatory cells, especially the rare polymorphonuclear leukocytes, and also contain a lesser number of other types of white blood cells, compared to the inflammatory cell populations in an acute inflammation site. A chronic inflammation site contains a significant number of macrophages, typically transformed from monocytes, which participate in a chronic inflammatory process. The inventors' studies suggest that it is not only the structure and cellular components but also the level of activity of plaque, particularly the macrophages, which makes it truly vulnerable to rupture. The macrophages in atherosclerotic plaques are not a homogeneous population, as also noted by Chien ("Molecular Basis of Cardiovascular Disease," W.B. Saunders Co., Philadelphia, Pa., pp. 355-356.) Some of the macrophages may be recent arrivals, others may be lipid-filled long-term residents of the plaque (sleepy macrophages—foam cells), and others may be apoptotic, accounting for considerable heterogeneity of a macrophage population. In addition to these features of vulnerable plaque, there is also a possibility that internal stimulators such as sudden intermittent contraction of plaque resulting from the effect of macrophage activity and chemical mediators on smooth muscle cells of relevant media may contribute to rupture by altering the external/internal hemodynamic balance.

Chronic inflammation sites, when sealed off by macrophages and fibroblasts, can change to an abscess which, invariably, is associated with a pathogen, i.e., bacteria, virus or chemical agents. In the case of vulnerable plaque, these pathogens may include high LDL, especially Ox-LDL, and infectious agents like *Chlamydia pneumonia, Helicobacetr pylori*, Herpes simplex virus, Cytomegalovirus and perhaps Influenza type A and Hepatitis A (which have been isolated from plaque), and a number of cytokines. The contribution of the infectious agents have not at this time been well established in atherosclerotic plaque. It has long been known that low oxygen, low pH, low glucose and high lactate are features of an abscess.

Taking the histopathological and biochemical features of atherosclerotic plaque into account, the inventors studies suggest that inflamed atherosclerotic plaque can be found by determining the presence of two or more of the following conditions at a site that is in question: high temperature, relatively low pH, hypoxia, presence of oxidant species and high oxidative stress (especially oxidized LDL), significant active macrophage population, thin plaque cap, senescence and/or apoptosis of smooth muscle or endothelial cells, low collagen content, intra plaque extravasation (rupture or leak of vasa vasorum), denudation of endothelial cells and the presence of microscopic amounts of thrombosis. The more information one has about one or more of these conditions at sites along the vessel wall, the better one can predict whether a site is a dangerous plaque that is in urgent need of intervention. These predictive conditions are determined by evaluating at sites along the vessel wall the various chemical and physical factors or parameters that are attributable to or associated with inflamed plaque, in combination with available visual and angiographic information. Such parameters, representative examples of which are discussed in more detail elsewhere herein, include oxyhemoglobin/deoxyhemoglobin, redox status of cytochrome oxidase enzyme $aa_3$; pH; glucose, lactate, oxidized metabolites of nitric oxide such as nitrosyl hemoglobin and nitrosyl tyrosine, and oxidized collagen levels; as well as other chemical factors that are characteristic of, or associated with chronic inflammation in plaque.

As used herein, the term "a parameter associated with inflamed vulnerable plaque" means a parameter found on, contained inside, emitted or evolved from, expressed by, attributable to or indicative of an atherosclerotic plaque having a region of active chronic inflammation, in a living vessel. For some of these parameters it is the quantitative, or relative amount with respect to another analyte, rather than the qualitative measure that is significant. For example, low pH as opposed to high pH, relatively low glucose and high lactate concentrations, high free radical and oxidant species concentrations. After thorough calibration and training with relevant standard methods it will be possible to define an exact measure of each parameter to permit more precise plaque prognosis.

By focusing in particular on the significant inflammatory component of the vulnerable plaques and the increased metabolic activity of certain cells associated with plaque, plaques are probed for particular functional or chemical characteristics. After ascertaining the qualitative or quantitative status of two or more of these characteristics or parameters, and then combining and comparing that information with other characteristics of the same site or other sites, and/or with preestablished calibration data for such characteristics in healthy or diseased vessels with plaques at various stages of risk, a more accurate estimation of the level of risk of a particular plaque site is determined than has been possible with existing methods. Initially, calibration data will be obtained from ex vivo measurements of the parameters in freshly excised plaque and vessel wall specimens.

Based on the referenced work with the thermal detection of inflamed vulnerable atherosclerotic plaques and on observations from ongoing ex vivo and animal studies using infrared and near infrared techniques, the present inventors have devised a method of detecting inflamed at-risk plaque which employs a non-destructive multi-parameter detection protocol and near-infrared catheter assembly, preferred embodiments of which are described in more detail below.

As mentioned in the background of the invention, active inflammation sites in the human body are usually characterized by increased release of cytokines and chemotactic factors, hypermetabolic status such as increased ATP consumption, low pH, increased oxygen species and free radicals, relatively low oxygen and glucose level and elevated lactate and other anaerobic metabolites, depending on the vascular performance of the site. The site is usually hotter than the adjacent area, which is perhaps due to increased metabolic activity mostly via a less efficient pathway (glycolysis), oxidative reactions involved in macrophage defense, and vasodilatation. Oxidized LDL is a strong stimulator of foam cell formation from macrophages, and is believed to play a substantial role in developing vulnerable plaques. Foam cell formation is minimal in the presence of native LDL. Modification of these lipoproteins, for example, by oxidation, is necessary for their binding to macrophage scavenger receptors. Oxidized LDL also has other characteristics such as cytotoxicity, chemoattraction for circulating monocytes, vasoconstriction, perturbation of the arachidonic acid cascade, involvement in haemostasis and immune mechanisms. In the conceptual diagram in FIG. 13 it is shown how ox-LDL may contribute to increased plaque activity and chronic inflammation.

Among the local key regulatory factors, nitric oxide (NO) released from active macrophages has an important role in control of the pathogens and/or other cells. In fact it is the oxygen free radical of this product, peroxynitrite, which is hyperactive and induces damage to the adjacent cells and tissue through lipid peroxidation. NO also has many metabolic and regulatory effects, which makes it a crucial component in regulation of endothelial function mainly vascular tone, macrophage activity, smooth muscle cell proliferation, platelet aggregation and thrombosis. Interestingly it has been recently reported that low pH regulates the expression of iNOS which is the main source of NO in inflammation sites produced by macrophages (Bellocq et al. *J Biol Chem* 273: 5086-5092 (1998)).

A high level of oxidative stress may increase the amount of oxidized protein in matrix and basement membrane specifically collagen at the site which might change the rate of degradation of these components. It is thought oxidized collagen might be poorly cross-linked and therefore susceptible to digestion by collagenase. It has been shown that fibroblasts penetrate in oxidized collagen faster. Fibroblasts penetrated faster in type IV/IIVox collagen gels than in normal type III+I collagen showing greater susceptibility of oxidized collagen. (Tiollier, et al. *Exp Cell Res* 191:95-104 (1990). In the case of oxidized collagen in atherosclerotic plaque cap, a poorer quality plaque cap results. Even though the collagen is plentiful and thick in a plaque cap, it still makes for a weak plaque cap that is susceptible to fissuring.

Cytochrome oxidase aa3, the terminal member of the intra-mitochondrial respiratory chain responsible for cell oxidation process, is usually hyperactive in these situations and its redox status is expected to be a good indicator of the oxidative stress of the cell.

Figure 2:
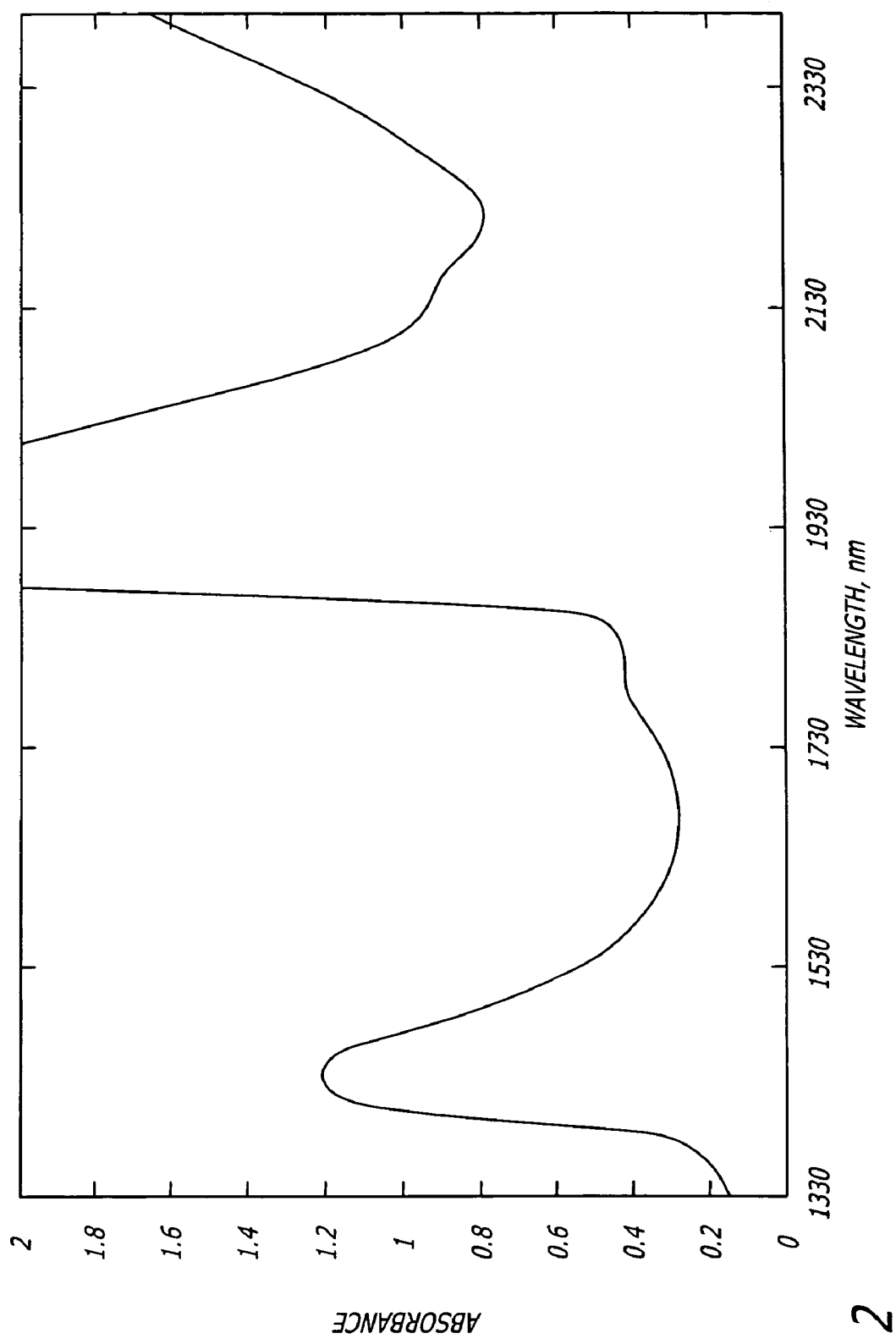
FIG. 2 is a prior art graph showing the near-infrared absorbance spectrum of histidine over the pH range 5-8.

The NIR spectra of various molecules may be used as indicators of the various parameter levels. For example, hemoglobin is a molecule with a strong spectral response to the presence of oxygen, as can be seen in the oxygenated and deoxygenated hemoglobin NIR absorbance spectra of FIG. 2 of Wahr, et al. in *J. Cardiothoracic and Vascular Anesthesia* 10:406-418 (1996). The strong absorbance of oxyhemoglobin at around 750 nm indicates that absorbance characteristics near this frequency in particular may be useful as an indication of oxygen levels. The cytochrome $aa_3$ enzyme molecule may also be used as an indicator of the oxidative stress of the cell. An example of the near-infrared absorbance spectra of oxidized and reduced cytochrome oxidase $aa_3$ ($Cytaa_3$) is also shown in Wahr, et al. (id). The strong absorbance of $Cytaa_3$ around 825 nm may prove to be a good indicator of oxidized cytochrome oxidase $aa_3$ in plaque. FIG. 2 shows that histidine has distinctive spectral responses to pH levels (see U.S. Pat. No. 5,355,880 (Alam, et al.)). Therefore, the shape of the hemoglobin histidyl absorption spectrum around 1300-2500 nm may serve as a good indicator of plaque acidity. Nitrosyl hemoglobin may also serve as an indicator of the level of nitric oxide metabolites in plaque. A representative NIR absorption spectrum for nitrosyl hemoglobin is reported by Ohdan, H. et al. *Transplantation* 57:1674-1677 (1994). Hydroperoxides and oxidized collagen may be measured as taught by Lippman (*Exp Geron* 20:1-5 (1985)) employing distinctive NIR wavelengths for hydroperoxide and for amide bonds. Glucose and lactate may be measured by near-infrared spectroscopy by adapting the method taught by McShane et al. (*Appl Spectrosc* 52: 1073-1078 (1998). Based on the earlier work described in Ser. No. 08/717,449, one physical characteristic expected of an inflamed, at-risk plaque is that it is hotter than the adjacent areas by about 0.2-4° C. In the case of a highly vulnerable plaque with a thin cap covering a large population of macrophages and a quantity of lipid, important associated physical and chemical parameters include a temperature differential of about 1.5-2° C., a pH of about 6-7.2, a significantly higher level of nitric oxide-related production of free radicals like peroxynitrate and -nitrite. As compared to "normal" or non-plaque vessel wall, active atherosclerotic plaques should also show higher activity rates of the enzyme cytochrome oxidase aa3. A quantity of low density lipoprotein, particularly oxidized LDL is also expected. Glucose availability to the cells in the plaque should be reduced and the lactate level elevated, compared to normal vessel wall, and compared to the more stable plaques. In contrast to prior art methods of plaque detection, a significant calcium content in a plaque could be indicative of a more stable, less vulnerable plaque, depending on the status of the temperature and chemical parameters at the site.

Accordingly, beams of visible and near-infrared wavelength radiation (i.e., approximately 400-2500 nm) are directed at successive sites along the interior vessel wall and the corresponding reflected spectra are received and analyzed such that the status of individual parameters within each site is ascertained by a suitably programmed processor. A multi-fiber optic bundle is used in the present example to accomplish the spectroscopic measurement of all or various combinations of the following factors in atherosclerotic lesions: oxyhemoglobin, pH, metabolites of nitric oxide (such as nitrosyl hemoglobin and nitrosyl tyrosine), oxidized cytochrome oxidase aa3, oxidized collagen, glucose and lactate. Preferably, remote visual monitoring of the same plaques is combined and correlated with the NIR measurements; and more preferably, angiographic data for the same site is also considered, if available.

Construction of a Multi-Parameter Catheter and Analytical Assembly

Figure 3:
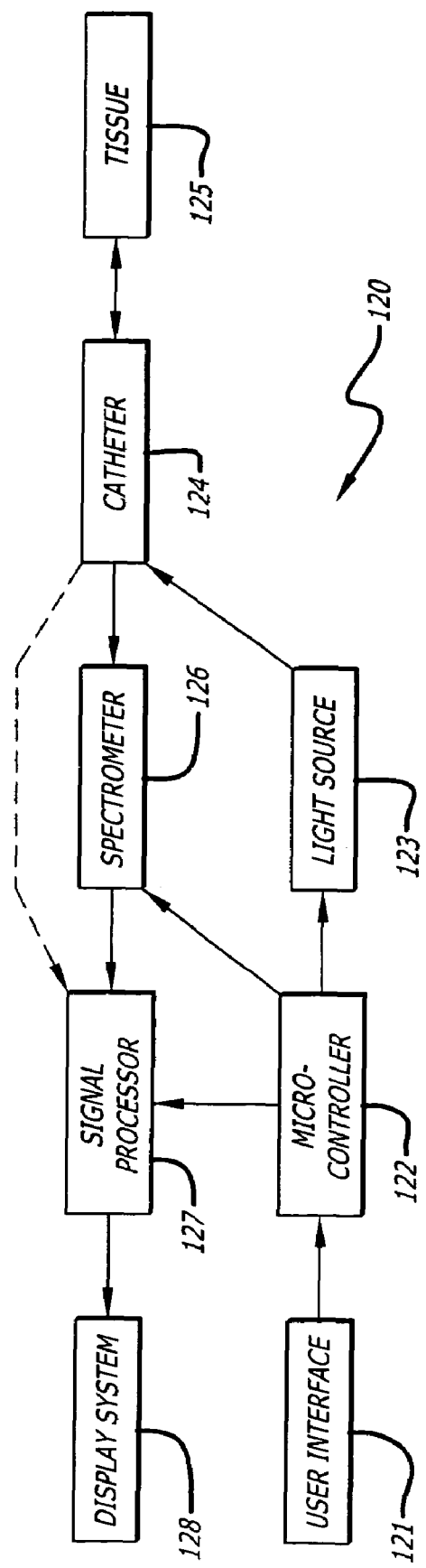
FIG. 3 is a schematic diagram of a fiber optic catheter apparatus in accordance with the present invention, as employed for detecting a vulnerable atherosclerotic plaque.

FIG. 3 shows a block diagram of one embodiment of a system 120 for detecting vulnerable atherosclerotic plaque in a living vessel. System 120 comprises a user interface 121, a microcontroller 122, a light source 123, a catheter 124, a spectrometer 126, a signal processor 127, and a display system 128. When catheter 124 is operatively positioned proximate to tissue 125 (best shown in FIGS. 6 and 7), a user may employ user interface 121 and display system 128 to test for various analytes or parameters associated with inflamed vulnerable atherosclerotic plaque in tissue 125. User interface 121 preferably includes a power switch and such other controls as may be needed for operating system 120. User interface 121 may operate in conjunction with display system 128 to provide menu-driven control of system 120. Microcontroller 122 implements a state machine for controlling the operation of light source 123, spectrometer 126, and signal processor 127. The microcontroller 122 may be a hardware implementation of a state machine, but is preferably a general purpose microcontroller which operates on software instructions stored in a nonvolatile memory (not specifically shown). Light source 123 is preferably a broadband light source such as a 66195 quartz-tungsten-halogen lamp from ORIEL, a company which is located at 250 Long Beach Blvd., Stratford, Conn. 06497.

Tissue 125 may be any site along a vessel wall, including "normal" vessel wall (which may be either a disease-free area or a benign fatty streaked area of vessel wall), areas of minimal and relatively stable plaque, and areas of intermediate to highly vulnerable atherosclerotic plaque. In alternative embodiments, tissue 125 is a body tissue other than a blood vessel wall which is capable of being contacted by the catheter as described above.

Catheter 124 transports light from light source 123 to tissue 125 and transports reflected light from tissue 125 to spectrometer 126. Catheter 124 preferably transports at least near infrared (NIR) light wavelengths between about 700 nm and 2500 nm, and may additionally transport visible light wavelengths between about 400-700 nm. Catheter 124 preferably comprises multiple strand optical fibers (optical fiber bundle) configured to image a circumferential slice of a living vessel. Suitable NIR optical fiber bundles include those of the Opti-Probe System from Foss NIR Systems, Inc. of 12101 Tech Road, Silver Spring, Md. 20904, and the IR Link™ Diffuse Reflectance System from Galileo of Galileo Park, Sturbridge, Mass. 01566. One suitable catheter implementation is discussed further below.

Spectrometer 126 is configured to detect intensities of various spectral frequencies of reflected NIR light from tissue 125. Spectrometer 126 may comprise a diffraction grating and a charge-coupled device (CCD) sensor for measuring the frequency spectrum of incoming NIR light. Preferably the spectral frequency intensities are also measured with a spatial component so that the spectral characteristics of different portions of tissue 125 can be individually determined. Examples of suitable spectrometers include the Cary 500 from Varian Instruments of 506 Julie Rivers Road, Sugarland, Tex. 77478, and the Opti-Probe System from Foss NIR Systems, Inc. of 12101 Tech Road, Silver Spring, Md. 20904.

The spectrometer measurements are provided to signal processor 127 which processes them to determine the presence and/or concentration (status) of various analytes or parameters in tissue 125. Signal processor 127 is preferably a general purpose digital signal processor which operates on the spectrometer measurements according to software stored in a nonvolatile memory (not specifically shown). Statuses which may be determined by signal processor 127 can include qualitative or quantitative levels of such basic parameters as: oxygen, metabolites of nitric oxide, pH, oxidized collagen, glucose, lactate, or another chemical parameter that is known to be associated with inflamed atherosclerotic plaque.

If desired, the processor may contain additional programming for evaluating various chemical and physical parameter data and making higher-level determinations or predictions about specific vessel sites. Such predictions or determinations may include, for instance, locations with hypoxia, low pH, appreciable concentration of oxidant species, high metabolic activity, significant active macrophage population, low structural rigidity, thin plaque cap, presence of microthrombi, leakiness, or presence of a fissure. The determination of the presence of these higher-level conditions obtains from algorithmically combining basic parameters levels. The signal processor may also generate an overall condition measurement such as probability of presence of a vulnerable plaque in tissue 125. By combining various basic parameter measurements together a more robust indicator of the presence of vulnerable plaque may be obtained, as discussed in more detail elsewhere herein.

The measurements and indicators generated by signal processor 127 are provided to display system 128 for viewing by the user, or may be output to a printer or in electronic format. One form of output may be desired over another for a particular situation. The measurements and indicators are preferably displayed in numerical form, although graphical image form may also be used. When catheter 124 is provided with a capability for transporting visible light, signal processor 127 may also process the visible light to generate a visible-light image of the interior of the vessel for display by display system 128. In alternative embodiments, the microcontroller 122 and signal processor 127 functions may be performed by a single processing unit.

In one embodiment, the signal processor 127 performs a multivariate regression technique to identify subtle changes in the collected NIR spectra related to the analytes of interest that may not be noticeable by visual inspection. To perform the multivariate regression a calibration data matrix R of spectral responses at selected wavelengths is first generated from a given set of calibration samples. The calibration data matrix R is then assumed to relate to a matrix of concentration values C by a model equation such as:

$$C=RS+E,$$

where S is a matrix of regression coefficients determined by the least squares method, and E is the residual error. The matrix of concentration values C is determined by an independent method of measuring analyte concentrations in the calibration samples. This model is the basis of the multiple linear regression (MLR) method. Other model equations may be employed, such as:

$$C=(RV)S+E,$$

where V is a matrix of eigenvectors of R chosen to "score" the indications of the analytes in a chosen eigenspace. This model is the basis of the principle component regression (PCR) method. The PCR method may be extended in a partial least squares (PLS) modeling procedure so that the underlying factors of both R and C are simultaneously estimated in an effort to provide a better predictive success. Each of these methods may employ a classical least squares cost function, thereby seeking to minimize the sum of the squares of the residual error E.

To identify a preferred method or model, a predictive residual error sum of squares (PRESS) procedure may be employed. In this procedure, two sets of calibration samples are employed. A first set (called the training set) is used to identify a regression coefficient matrix S. The second set is analyzed by the model to determine a matrix of estimated (predicted) concentration coefficients C. The estimated concentration coefficients matrix is compared with the independently measured concentration coefficients, and the method which yields the smallest sum of squares of the errors between the predicted and measure concentration coefficients is selected as the preferred method. More details regarding these methods and the selection procedure can be found in standard reference texts such as:

Edward V. Thomas, "A Primer on Multivariate Calibration," *Analytical Chemistry*, 66:795A-804A, 1994.

Kenneth R. Beebe and Bruce R. Kowalski, "An Introduction to Multivariate Calibration and Analysis," *Analytical Chemistry*, 59:1007A-1017A, 1987.

Chris W. Brown and Robert J. Obremski, "Multicomponent Quantitative Analysis," *Applied Spectroscopy Review*, 20:373-418, 1984.

Once a model has been chosen and a matrix of regression coefficients S identified, an analyte concentration coefficient vector c may be calculated by signal processor 127 from a spectral frequency measurement vector r:

$$c=rS \text{ (for the MLR method), or}$$

$$c=r(VS) \text{ (for the PCR method).}$$

It is observed that in one embodiment, the coefficient matrix C and vector c represent concentrations of analytes such as oxyhemoglobin, deoxyhemoglobin, nitrosylhemoglobin, oxidized cytochrome oxidase $aa_3$ ($Cytaa_3$), and reduced $Cytaa_3$, as indicated by spectral analysis. In another embodiment, the coefficient matrix C and vector c may represent various condition levels such as pH level, oxygen level, macrophage density, level of nitric oxide metabolites, oxidized species level, glucose, lactate, and collagen concentrations, or higher-level conditions such as extent of cellular metabolic activity, macrophage population, and plaque structural rigidity. In each case, the calculated coefficient vector c values may be provided to display system 128 along with a predictive index value P for viewing by a user. The predictive index value P is a percentage value which indicates the likelihood of the presence of vulnerable plaque in the tissue 125, and is calculated from the coefficient vector c according to a linear or heuristic model. The system 120 is proposed to develop and test various models for generating the predictive index value P.

Multi-Parameter Catheter

FIG. 4 shows an overall view of one embodiment of catheter 124. Catheter 124 has a distal end portion 131 (located inside the body during use) connected to conduit 133 by neck portion 132. Conduit 133 (partially disposed inside the body during use) couples distal end portion 131 to proximal end portion 134 (located outside the body during use). Proximal end portion 134 terminates in connectors 135.

FIG. 5 shows proximal end portion 134 in more detail. Connectors 135 include an illumination connector 141 and detection connector 142, and may further include an inflation connector 143 and a flushing connector 144. Preferably an aperture 145 is provided in manifold 146 of proximal end portion 134 for a guide wire to pass through. Illumination connector 141 is configured to couple to light source 123 to transport light to the distal end portion 131, and detection connector 142 is configured to couple to spectrometer 126. Inflation connector 143 is configured to couple to a balloon inflation source (not shown) and flushing connector 144 is configured to couple to a fluid source (also not shown). The balloon inflation source preferably provides air at a variable pressure, and the fluid source is preferably a flushing or perfusion medium such as isotonic saline or blood.

Figure 9:
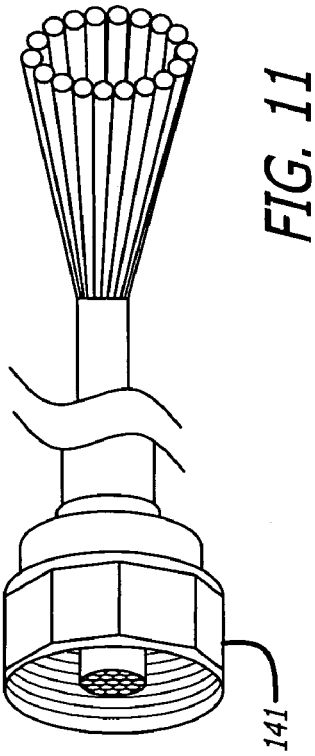
FIG. 9 is a cross-sectional view of the main body of an embodiment of the catheter of FIG. 4.

FIG. 9 shows a cross-sectional view of one embodiment of distal end portion 131. Distal end portion 131 is placed inside a living vessel such as an artery. Arterial walls 151 are shown surrounding the catheter surface 152. The annular space between arterial walls 151 and surface 152 is sealed by a balloon 153 which is inflated via an inflation aperture 154. A layer of optical fibers 155 oriented parallel to the axis of distal end portion 131 provides illumination to a mirror 160. Mirror 160 reflects the illuminating light through transparent window 161 onto arterial wall 151. Light from arterial wall 151 passes through window 161 and is reflected by mirror 160 into a layer of optical fibers 156 oriented parallel to the axis of distal end portion 131. Distal end portion 131 also includes an inflation lumen 157, a wire lumen 158, and a flushing lumen 159, each located radially inward from the optical fiber layers and oriented parallel to the axis of distal end portion 131. The inflation lumen 157 is connected to the interior of balloon 153 via inflation aperture 154. The wire lumen 158 terminates at guide wire aperture 162 of distal end portion 131, and the flushing lumen 159 terminates in one or more flushing apertures 163 proximate to the end of distal end portion 131. Window 161 is preferably a flexible, inert, and transparent polymer plastic material suitable for directly contacting the surface of a plaque or vessel wall 125 and shielding the distal ends of the optical fibers.

Figure 7:
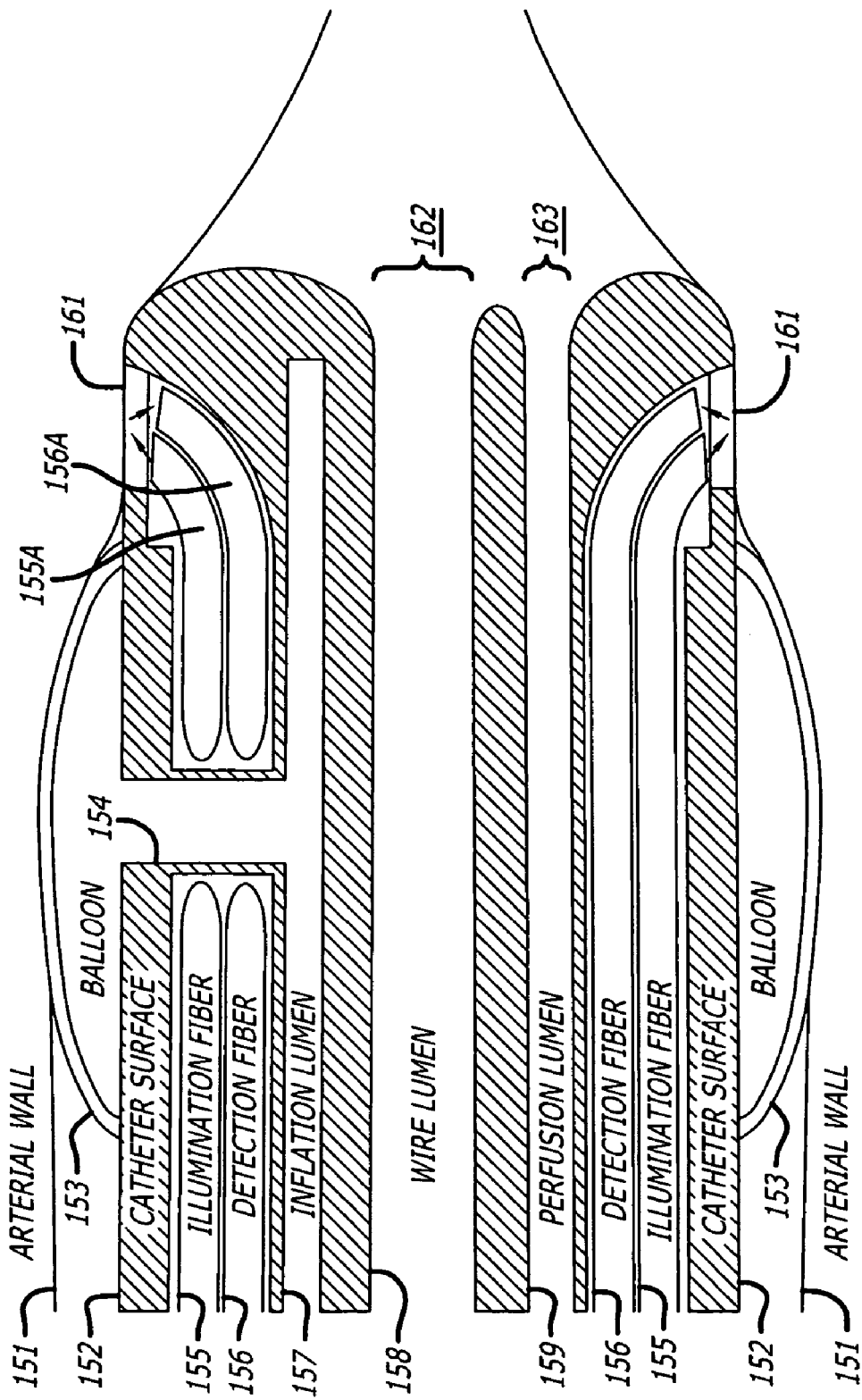
FIG. 7 is a cross sectional view of the catheter tip of an alternative embodiment of the catheter of FIG. 4.

FIG. 7 shows a cross-sectional view of a second embodiment of distal end portion 131. In this embodiment the individual fibers of optical fiber layers 155 and 156 are bent radially outward at their distal ends 155A, 156A. Light from illumination fibers 155 is directed onto arterial walls 151 through window 161. Light reflected from arterial walls 151 passes through window 161 into detection fibers 156 and is conveyed by the detection fibers 156 back to spectrometer 126. Incident and reflected light is indicated in FIG. 7 by arrows. For some applications, the bent tip embodiment might be preferred over the straight-tip-with-mirror embodiment. For ease of manufacturing, some users may prefer the straight tip version.

Figure 8:
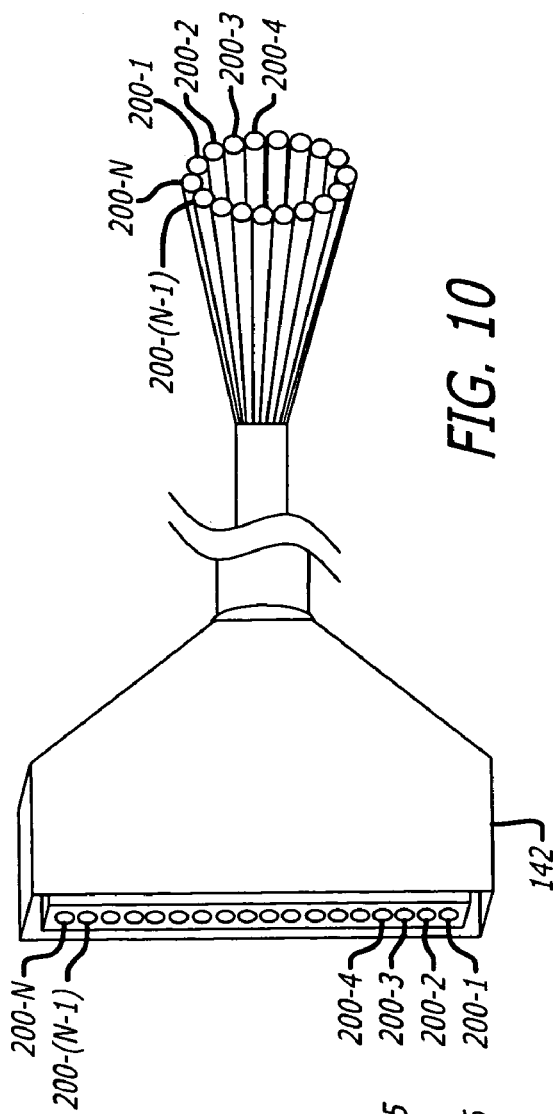
FIG. 8 is a partially cut away view of an embodiment of the catheter of FIG. 4 showing a transition joint.
Figure 10:
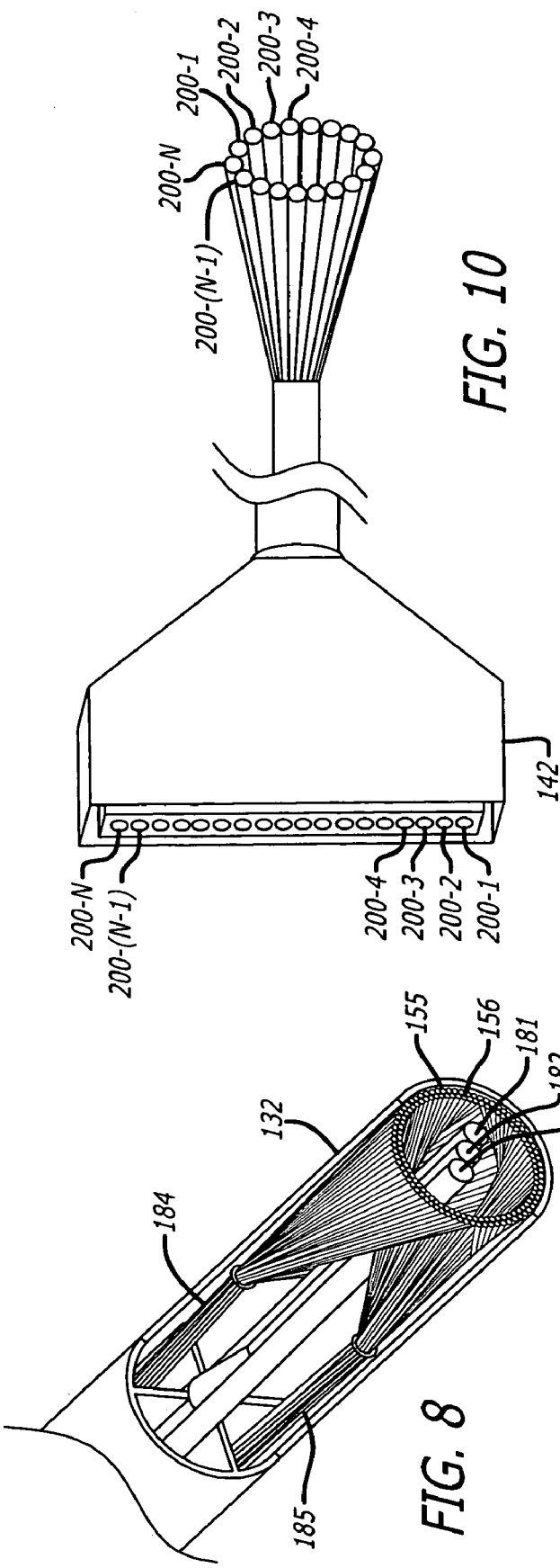
FIG. 10 is an enlarged illustration of one embodiment of the detection fiber bundle of FIG. 4, showing the relationship between the individual fiber proximal and distal ends of the detection fiber bundle.
Figure 11:
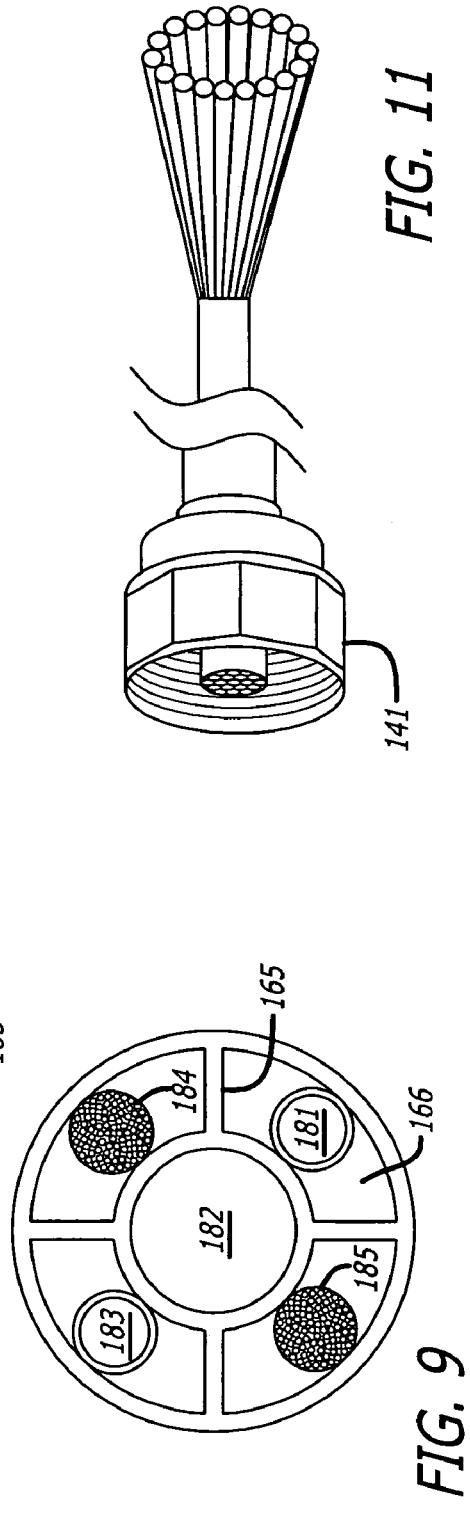
FIG. 11 is an enlarged illustration of one embodiment of the illumination fiber bundle of FIG. 4 showing the relationship between the proximal and distal ends of the illumination fiber bundle.

FIG. 8 shows an embodiment of neck portion 132. The illumination fibers 155 are gathered from their circumferential positions into a fiber bundle 184, and the detection fibers 156 are gathered into fiber bundle 185. Inflation lumen 181, wire guide lumen 182, flushing lumen 183, illumination fiber 184, and detection fiber 185 are each shown entering a divided portion of conduit 133. A cross-sectional view of conduit 133 is shown in FIG. 9 to illustrate one embodiment of the spatial relationship of the inflation lumen 181, wire guide lumen 182, flushing lumen 183, illumination fiber 184, and detection fiber 185 along the length of catheter 124. The wire guide lumen passes along the central axis of conduit 133, and the annular space between the wire guide lumen 182 and the outer surface of the catheter 124 is divided by radial walls 165 that run substantially the length of conduit 133. In the divided annular spaces 166 the illumination and detection fibers are placed, as well as the inflation lumen and flushing lumen when they are present. Although the inflation and flushing lumens are shown as tubes within the divided annular segments, it is understood that the entire divided segment can be used as a lumen for transporting the inflation or flushing media, for ease of construction. The flushing lumen may be used for transporting a perfusion medium rather than a flushing medium where it is necessary to maintain blood flow through the vessel undergoing examination. FIG. 10 shows the relationship between the distal and proximal ends of detection fiber 185. Detection fibers of fiber bundle 185 are not a "coherent" fiber which couples to spectrometer 126 via connector 142. The individual optical fibers 200-1 through 200-N are arranged in order around the circumference of catheter 124 at the distal end 131, and this ordered spatial relationship is preserved by connector 142. Conversely, the illumination fibers of bundle 184 shown in FIG. 11 are not necessarily coherent fibers, and connector 141 is not necessarily configured to provide distinguishable access to any particular fiber. Rather, all fibers are uniformly used to carry illumination from light source 123 to tissue 125.

Preferably the multi-parameter catheter system includes means for visible wavelength monitoring of the color and physical appearance of plaque and the vessel wall surface as the catheter is moved within the vessel. It is particularly desirable to be able to ascertain by colorimetry, the presence or absence of yellow (a sign of carotene-pigmented deposits of cholesterol), white or red (microthrombi, hemorrhage) in the same areas undergoing examination by near-infrared spectroscopy, as discussed in more detail below. Visual inspection may also reveal areas of marked plaque erosion though it may not accurately identify endothelial denudation. Endothelial cells of the plaque, which are the most active and multifunctional layer of the artery, provide several important functions, the most important of which is prevention of blood clot formation. It has long been known that when the endothelial layer of atherosclerotic plaque, for various reasons, fails to properly fulfill this pivotal job, an increased tendency occurs for clot formation over the plaque area. Superimposed on an otherwise narrowed artery, the additional clot formation can result in complete occlusion and clogging of the artery. This model is typical of atherosclerotic disease in which significant narrowing (90% or more) plays a major role, especially coronary artery disease, and is supported by an abundance of pathologic and angiographic evidence.

Supplemental visual monitoring allows the physician to make an independent analysis of atherosclerotic plaque detected by the NIR analysis of multi-parameter catheter system 120. To this end, illumination and detection fibers 184, 185 may be configured to transport visible wavelengths, and signal processor 127 may be configured to generate a graphical image of the vessel wall surface for display system 128. In an alternative embodiment a separate visible imaging bundle (not shown) that can be introduced through the guidewire lumen after the catheter is inserted and the guidewire removed. At their proximal ends, these fibers are coupled to a visual imaging system which may be separate from multi-parameter catheter system 120 or may be integrated into the multi-parameter catheter system 120. In order to keep the circumferential dimension of the catheter conduit 133 to a minimum, it is preferred that the visible imaging and the NIR detection capabilities share the same fibers.

Figure 6:
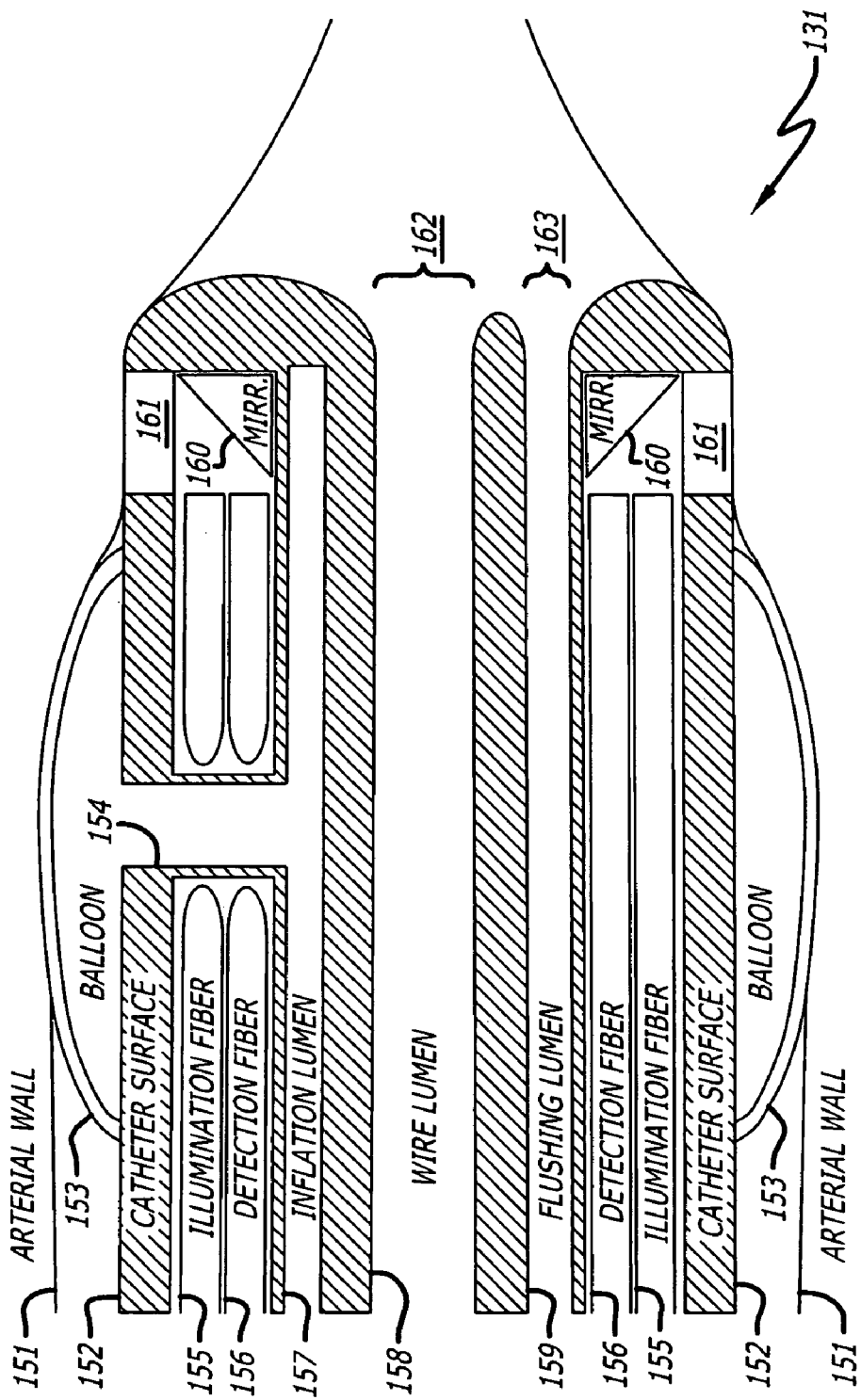
FIG. 6 is a cross-sectional view of the catheter tip of one embodiment of the catheter of FIG. 4.

The conduit 133 of catheter 124 is of suitable dimension to permit it to slide onto a standard arteriography guidewire, which can be surgically inserted into a patient's artery. The guidewire would extend proximally from aperture 145 (shown in FIG. 5) and distally from aperture 162 (FIGS. 6 and 7). The guidewire extends through guidewire lumen 182 (FIG. 9), which is preferably centrally located in catheter 124.

The materials of which catheter 124 is constructed are similar to conventional angioscopy catheters and may be any suitable biocompatible material, including flexible plastics such as nylon, TEFLON, vinyls such as polyvinyl chloride, polyurethane, and polyethylene, or any of various rubber compounds. The catheter is preferably of similar diameter and length to conventional angioscopy catheters. Several options for materials for the other various components of the catheter devices described herein exist. Key considerations for choosing suitable optical components are optical transparency, flexibility and strength. Materials such as high strength polyester and polyethylene terephthalate (PET) are very clear and easily extruded in ultrathin wall sizes. A high strength braided polyester is useful for translating twisting motions over long distances as may be required in certain embodiments. Spacers/bearings can be made from TEFLON. The overall flexibility of the catheter will be approximately the same as similar-sized cardiovascular laser, fiberoptic, angioplasty and atherectomy catheters. These devices should therefore be deliverable to even small diameter coronary arteries.

The balloon 153 is made of an elastic material and is similar to that used in conventional arterioscopy catheters such as described in U.S. Pat. No. 5,728,068. The perimeters of balloon 153 are such that inflation can produce sealing or annular closure between catheter 124 and the interior of the vessel wall.

Detection of a Vulnerable Plaque

Catheter 124 is inserted into a patient's artery by way of a guidewire, substantially the same way as with other arterioscopy procedures. Optionally, the balloon may be used to assist in flow-directed movement through the vessel. The guidewire is used to guide the placement of distal end 131 of catheter 124 to an area of the artery that is of interest, particularly where atherosclerotic plaques are situated on a vessel wall. As is the case with typical arteriography procedures, the level of risk of rupture of any particular plaque locus or the likelihood of a thrombus forming at a particular locus in the artery is substantially unknown at the outset of the procedure.

Inflatable balloon 153 (shown in FIGS. 6 and 7 in inflated condition) is inflated to cause it to rest firmly against an interior wall of an artery and against any plaque loci. Inflation of balloon 153 substantially limits flow of blood downstream of the contact points between the balloon and the artery wall. If desired, blood may be transfused through flushing lumen 159, or a flushing fluid such as saline can be introduced, while the vessel is undergoing examination. By advancing or retracting the catheter, as needed, the transparent window 161 is situated adjacent a circumferential section or slice of the vessel wall, which may include an atherosclerotic plaque or a non-diseased area.

The status of one or more chemical parameters at discrete sites at intervals along a vessel wall are measured as described in more detail below, and the measurements are then used to indicate or predict the vulnerability of a particular site to rupturing or to formation of a thrombus. The dimensions of each site generally correspond to the boundaries of the field of view, or illumination sector of one optical fiber. Measurements are made at intervals along the vessel wall, as the catheter is withdrawn at the desired rate. Inflated balloon 153 is disposed immediately "upstream" from the window 161 on catheter 124. One important purpose of balloon 153 is to avoid interference problems associated with absorption and scattering of NIR radiation by blood or perfusion fluid between the tissue 125 being analyzed and the optical fibers 155, 156. Balloon 153 upon deflation retreats from its contact of the arterial wall, allowing reestablishment of natural blood flow within the artery, and allowing facile movement of catheter 124 in the artery to a next position, for instance to a position at which catheter apparatus 120 may be used to measure NIR spectra reflected from another plaque locus. Inflation/deflation of balloon 153 may be accomplished in any of a number of ways known well to those of skill in the art of building angioplasty or embolectomy catheters or balloon-tipped catheters.

Upon inflation and contact of the artery wall, the balloon 153 blocks the blood flow and allows the vessel wall to rest against the catheter's distal end 131. NIR radiation from illumination fiber 155 illuminates the tissue 125, in cooperation with mirror 160 or fiber bent tips 155a. Reflected light arising from the irradiated sites is received by the array of detection fibers 156, assisted by a focusing mirror 160 or by bent fiber tips 156a, and transported by detection fiber 156 to spectrometer 126 and processor 127 for analysis.

At the same time that the NIR examination of the vessel wall is going on, or in cooperation with NIR examination, a detailed visible color image of the wall may also be monitored, or the visible wavelength light is employed for calorimetric analysis, particularly for the purpose of detecting microthrombi associated with inflamed plaque and white clots from fresh red ones, as discussed in more detail below. Visible light wavelengths carried by detection fiber 156 or by a separate fiber may be processed by system 120 to produce a visible color image of the same area currently undergoing NIR examination. The physician may use the additional information to assist in diagnosing the status of the tissue. The exemplary procedure described above is directed to the examination of a patient's artery or other vessel which is of a size which permits catheterization. However, with only minor modification of the apparatus and procedures a similar apparatus can be employed to examine another vessel or organ of the body to distinguish and evaluate sites of active metabolism or inflammation, such as sites of infection, cancer, wounds or auto-immune disease, for example.

Referring again to the schematic diagram of FIG. 3, in one embodiment of system 120, the spectrometer 126 comprises a diffraction grating and a charge-coupled device (CCD). When NIR light from detection fibers 200 (FIG. 10) introduced into spectrometer 126 the different frequencies (wavelengths) of the input NIR light will be dispersed by the diffraction grating onto the CCD detector. The CCD is positioned to detect the distribution of diffraction peaks, and thereby determine the frequency spectrum of the NIR light. The CCD is preferably a two-dimensional array of light intensity sensors so that a frequency spectrum can be found for more than one fiber or group of fibers at a time. Referring momentarily to FIG. 10, the detection fibers 200 are preferably divided into four groups (e.g. 200-1 through 200-N/4, 200-(N/4+1) through 200-N/2, 200-(N/2+1) through 200-3N/4, and 200-(3N/4+1) through 200-N), each group covering 90 degrees of arc. Each of these four fiber groups are spaced vertically (along the y axis) with respect to the CCD, and the diffraction grating is arranged to disperse the first order interference peaks of each group horizontally (along the x axis) across the CCD detection surface. The number of fiber groups may be increased or decreased to alter the circumferential resolution of the NIR spectral analysis.

The CCD measures the intensity of light at the various NIR wavelengths to determine a frequency spectrum for each fiber group. In one embodiment, the signal processor 127 takes these measured frequency spectra and performs some matrix multiplications to determine the tissue conditions within the detection area of each fiber group.

Some of the chemical parameters that are contained in or locally associated with inflamed, vulnerable plaque and which can be detected and quantified in a living vessel include the following:

Oxyhemoglobin/Deoxyhemoglobin

The application of near-infrared spectroscopic (NIRS) technique in continuous, non-invasive, bedside monitoring of blood oxygen saturation has been very well known for years. These instruments use principles of near infrared light transmission or reflection to measure the concentrations of oxygenated hemoglobin ($O_2Hb$) and deoxygenated (reduced) hemoglobin (RHb) in tissue. NIRS is based on relatively simple principles. First, each molecule that exists in the real world has its own characteristic and unique absorption spectrum. For example, water and hemoglobin absorb at totally different wavelengths in near-infrared (NIR). Second, the amount of absorption is proportional to the concentration of the substances in the sample. This makes quantitative measurement using near-infrared spectroscopy (NIRS) techniques possible.

The attenuation of the transmitted radiation by an absorbing sample is described by the Beer-Lambert law. This states that the fraction dP/P of radiant energy P absorbed by an infinitesimal thickness of sample is proportional to the number of molecules dn in that thickness, that is $$-dP/P = k\,dn$$

where k is a constant.

Assuming that the sample thickness is 1 and concentration of the interested molecule is c, one can derive the relation between the initial energy $P_0$ and transmitted energy $P_T$ $$\mathrm{Log}(P_0/P_T)=klc$$

Experimentally, the fraction of radiation $(P_T/P_0)$ transmitted by the sample is measured and this is called the transmittance (T). In practice, the transmittance is converted to the absorbance (A) which is defined by $$A=\log(l/T)=\log(P_0/P_T)$$

or $$A=klc$$

The partial pressure of oxygen ($PO_2$) in tissues need only be about 3 mm Hg to support basic metabolic demands. This tissue level, however, requires capillary $PO_2$, to be near 40 mm Hg, with a corresponding arterial $pO_2$ of about 95 mm Hg. Most of the oxygen carried by blood is stored in red blood cells reversibly bound to hemoglobin molecules. Oxygen saturation ($SaO_2$) is defined as the percentage of hemoglobin bound oxygen compared to the total amount of hemoglobin available for reversible oxygen bounding. Although endogenous molecular oxygen is not easily detectable by NIRS, hemoglobin serves as an oxygen sensitive "dye" such that when oxygen reversibly binds to the iron atom in the large heme prosthetic group, the electron distribution of the heme is shifted, producing a significant color change. The optical absorption of hemoglobin in its oxygenated and deoxygenated states is shown by Wahr et al. (*J Cardiothorac Vasc Anesth.* 10:406-418 (1996); and in FIG. 1 of Ohdan, H. et al. (*Transplantation* 57:1674-1677 (1994). Fully oxygenated blood absorbs strongly in the blue and appears bright red; deoxygenated blood absorbs throughout the visible region and is very dark (appearing blue $$SaO_2 = \frac{O_2 Hb}{RHb + O_2 Hb} \times 100\%$$

when observing through tissue due to light scattering effects). The optical absorption spectra of oxyhemoglobin ($O_2Hb$) and "reduced" deoxyhemoglobin (RHb) differ substantially. It is this difference which provides the basis for spectroscopic determinations of the proportion of the two hemoglobin states.

Redox State of Cytochrome Oxidase aa3

In a cell, cytochrome aa3 is the terminal receptor enzyme for oxygen in the electron transport chain. When oxygen supply within the cell is inadequate, the rate of electron transport is reduced, and oxidative phosphorylation decreases, leading ultimately to anaerobic metabolism. NIRS measurements provide the means to determine the intracellular oxidative processes. Cytochrome aa3 contains four redox active metal centers. One of these, the binuclear $Cu_A$ center, has a strong absorbance in the NIR that enables it to be detectable in vivo by NIRS. Unlike the case with deoxyhemoglobin and oxyhemoglobin, concentration changes of the total cytochrome oxidase protein occur very slowly (over days). However, the copper center rapidly accepts and donates electron, and can change its redox state quickly. This redox change is detectable by NIRS. The NIR absorbance spectrum of cytochrome $aa_3$ has been determined by others, see FIG. 3 of Wahr et al. (id). Deoxyhemoglobin, oxyhemoglobin and cytochrome $aa_3$ are measured substantially as described in U.S. Pat. No. 4,281,645 (Jöbis), modified however for use with the new NIR catheter assembly described above.

pH pH and Plaque Rupture

Figure 13:
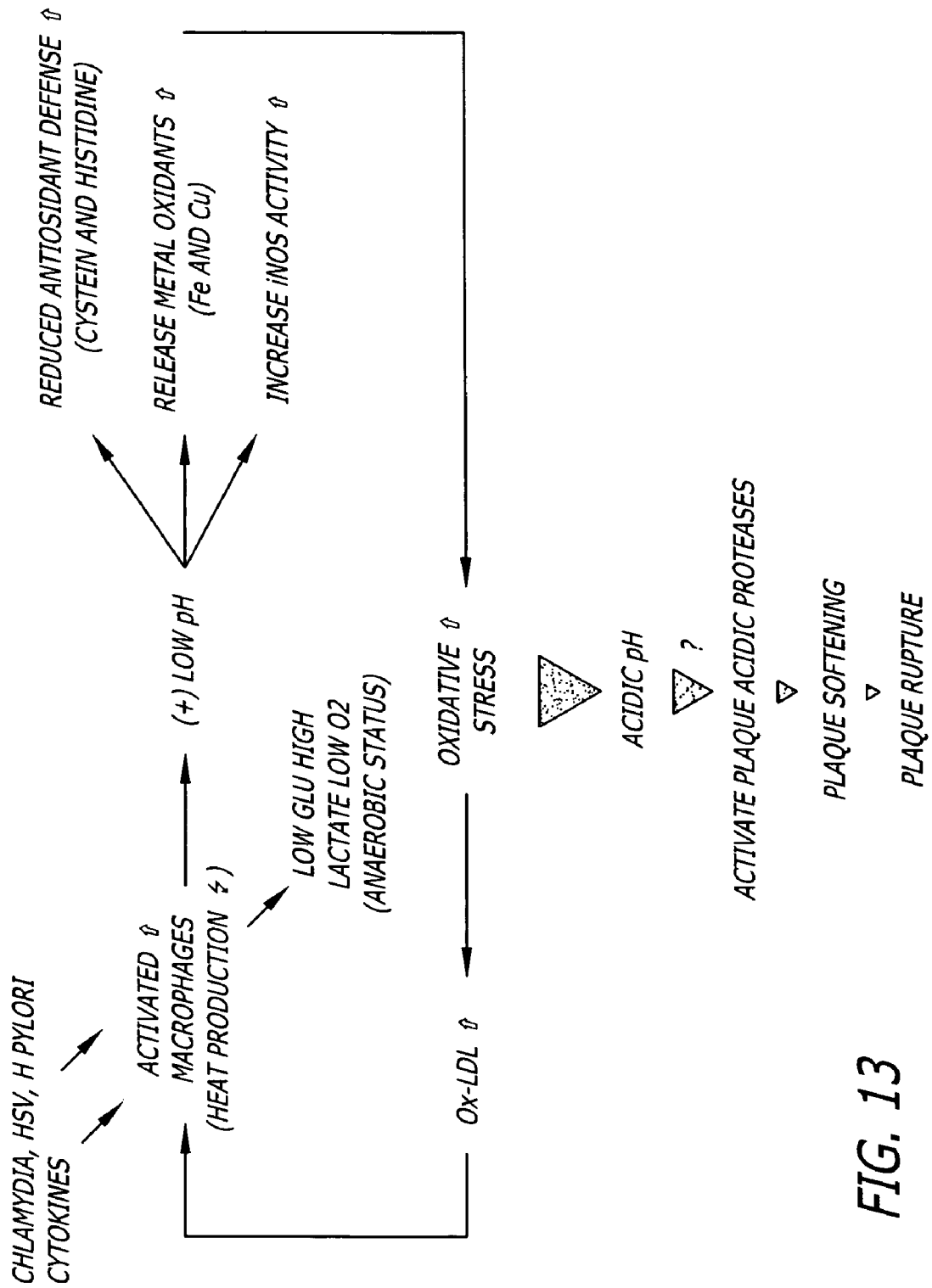
FIG. 13 is a diagram illustrating conceptually the feedback cycle of low pH and elevated oxidant species which induce atherogenesis.

Applicants predicted that acidified plaque is a prime indicator of vulnerable, rupture-prone atherosclerotic plaque, and is detectable and quantifiable using the NIR catheter assembly of the invention. The presence of acid pH conditions in at-risk plaque is also supported by the observation of others. For example de Vries et al. have reported that oxidized LDL-activated macrophages lead to acidification of the extracellular pH (*FASEB J* 12:111-118 (1998)). We think it is likely that a vicious cycle develops in vulnerable atherosclerotic plaque in which factors such as infiltrated macrophages, oxidized LDL (ox-LDL), intracellular and extracellular anti-oxidant components, and oxidant ions play a substantial role in perpetuating low pH and high oxidative stress conditions. Perhaps apoptosis, necrosis, foam cell degradation and subsequent release of long chain fatty acids into free fat pool of the plaque are important as well. Going beyond the concept that vulnerable plaque comprises an inflamed area in which a significant infiltration of activated macrophages results in low pH, high oxygen species, high lactate and perhaps low oxygen and glucose, we suggest a possible mechanism in which positive feedback results in a self-perpetuating cycle of low pH and high oxidative stress leading to plaque progression and eventual rupture or thrombus formation, as illustrated in the diagram shown in FIG. 13. As mentioned above, oxidized LDL the key component of abnormal fat metabolism in developing foam cell can greatly stimulate macrophages. In fact, infiltrated macrophages become metabolically highly activated by taking up ox-ODL. As a result the activated macrophages metabolize glucose at a greater rate, and excrete acidic metabolites such as lactate and $CO_2$, leading to acidification of both intra and extra cellular pH. Low pH, in turn, tends to sustain the oxidative stress (i.e. ox-LDL) perhaps by reducing antioxidant protection offering by intracellular glutathione system or extracellular thiol and imidazole-containing amino acids (cysteine and histidine) or by increasing detachment of oxidative ions (Fe and Cu) from their binding proteins (transferrin and ceruloplasmin), as generally illustrated in FIG. 13. In FIG. 13, "iNOS" is inducible nitric oxide synthase and "HSV" indicates herpes simplex virus.

The possibility of reducing anti-oxidative protection of cell and plasma in low pH has been consistently demonstrated by others, confirming the lower pH and the higher oxidation rate of LDL by copper and iron and the lower antioxidant effect of serum mediated by thiol and imidazole containing amino acids (cysteine and histidine). Since a significant part of the normal extracellular antioxidant defense mechanism is reduced in an acidic environment, establishment of a cyclic sequence such as this could account for a continuous supply of ox-LDL to the macrophages and maintenance of a lowered pH environment in the plaque. Having increased macrophage acidic protease activity in this low pH environment, low pH should be a good predictor of impending plaque rupture. Low pH might be considered to be a marker, rather than an independent predictor, showing sustained inflammation and macrophage infiltration, oxidative stress and perhaps apoptosis and necrosis. Within an at-risk atherosclerotic plaque, regions of pH heterogeneity may exist somewhat akin to temperature heterogeneity, which has previously been correlated with inflamed macrophage-rich areas in vulnerable atherosclerotic plaque.

pH and Matrix Digesting Enzymes

It has also been suggested that active matrix metalloproteinases (MMP) (mainly collagenase, gelatinase and elastase) play significant roles in plaque rupture via breaking down the protein skeleton of the plaque (see, e.g., Gacko et al. *Clin Chim Acta* 23:171-7 (1998)). Although matrix metalloproteinase activity is thought to be optimum at neutral pH, (indeed they are able to maintain a proteolytic activity at neutral pH, in contrast to other digesting enzymes which typically function in acidic pH conditions), it is likely both MMPs (specially MMP3) and a large group of macrophage-derived acid proteases could contribute to matrix digestion in acidic pH. Here it is expected that acidic macrophage-derived proteinases would exercise a significant part in proteolysis and softening of atherosclerotic plaque. Ongoing investigations are aimed at elucidating the activity of matrix metalloproteinases and acidic proteases in at risk plaque and their associated pH environment. Preliminary investigations performed in carotid endarterectomized plaque appear to confirm this hypothesis.

As discussed in the background above, near-infrared spectroscopy can be employed to measure secondary spectroscopic effects of the hydrogen ion. Adapting the NIR methodology described by Alam et al. in U.S. Pat. No. 5,792,050 for measuring tissue pH in vivo, and modifying it for use with the NIR catheter assembly of the present invention, the pH of atherosclerotic plaque is determined based on absorbance spectra of the hemoglobin histidyl rings in the physiological pH range of 6.8 to 7.8. FIG. 2 shows the NIR absorbance spectrum for histidine, as determined by Alam et al. The disclosure of U.S. Pat. No. 5,792,050 is incorporated by reference to the extent that it provides methods and materials not specifically set forth herein. Radiation in the wavelength range 700-2500 nm is directed onto a site along a vessel wall. In atherosclerotic plaque, the smooth muscle cells are supplied with blood by vasa vasorum, so the hemoglobin supply is adequate for NIR measurements. The slower diffusion rate inside a plaque, compared to that of the circulating blood or highly perfused tissue, actually enhances the opportunity to detect regions of pH heterogeneity in plaque by NIR measurement.

Another alternative way of measuring pH in a tissue is based on the fact that red blood cells change shape as the pH of the surrounding media is varied. This shape change causes the NIR light scattering properties to change. NIR spectroscopy can be employed to measure changes in light scattering and correlate the scattering with pH changes. Accordingly, the pH can be determined by evaluating the light scattering properties of red blood cells in plaque and comparing and correlating these values to standard pH values for red cells, similar to the method described by Robinson, M. R., et al. *Clin Chem* 38:1618-1622 (1992), with the necessary modifications for using the NIR catheter described above.

Non Invasive Monitoring of Plague pH using MR Imaging and Spectroscopy

In another alternative embodiment, in which the NIR fiber optic catheter is omitted, the pH parameter can be measured non-invasively in plaque by magnetic resonance (MR) spectroscopy, similar to the techniques described in Matthews et al. (Ann Neurol 29:435-8 (1991), Houston, et al. (Adv Exp Med Biol 428:253-9 (1997), Pirttila et al. Neurosci Lett 178: 111-4 (1994), Larcombe-McDouall et al. Pflugers Arch 435: 810-7 (1998), Hunjan et al. Magn Reson Med 39:551-6 (1998), or U.S. Pat. No. 5,753,207 (issued to Zuo et al). Magnetic resonance spectroscopy offers a sensitive method to measure tissue pH (0.02). There are several probes, such as Lanthanide complexes, for example, that may be used for this measurement. Some of the ongoing studies by the inventors are directed at detecting atherosclerotic vulnerable plaque using non-invasive MR spectroscopy technique, focusing on both temperature and pH in addition to the plaque's anatomical features.

Other alternative techniques for measuring pH of tissue include chemiluminescence, ultraviolet fluorescence-induced and natural spectroscopy, and infrared reflectance spectroscopy, each of which can be accomplished using the fiber optic catheter assembly of the invention and appropriate algorithms and modifications, in order to measure the pH of plaque. Each of these techniques is well known in the art with respect to interrogation of tissue other than atherosclerotic plaque. (See, for example, Kneen et al. *Biophys J* 74:1591-9 (1998); U.S. Pat. No. 5,302,731 (issued to Pitner et al.); Dellian et al. *Br J Cancer* 74:1206-15 (1996); and U.S. Pat. No. 5,708,275 (issued to Rhodes, M. L.)).

Nitric Oxide and its Metabolites

Among the known local inflammatory factors, nitric oxide (NO) released from macrophages and polymorphonuclear leukocytes (PMNs) has an important role in control of pathogens and/or other cells. In fact, it is the oxygen free radical of this product, peroxynitrite, which is hyperactive and induces damage to the adjacent cells and tissues through lipid peroxidation.

It is well known that nitric oxide (NO) is produced through an L-arginine oxidative pathway in many types of mammalian cells, since it is involved in vascular tone, platelet aggregation, neurotransmission and immune activation. NO is synthesized from L-arginine and molecular oxygen by a group of newly discovered enzymes, the NO synthases. Nitric oxide is notoriously noxious because of its free-radical structure: it possesses an extra electron, making it highly chemically reactive. NO is extremely labile, or short-lived. Therefore, continuous non-invasive measurements of NO are difficult to make in vivo. In disease states characterized by high NO synthase activity, the iron in hemoglobin becomes nitrosylated since the affinity of $HbO_2$ for NO is $10^6$ times greater than its affinity for $O_2$. NIRS can provide the quantitative measurement of NO through nitrosyl hemoglobin (Hb—NO) (see Ohdan H. et al. (*Transplantation* 57:1674-1677 (1994); *Transplantation* 60:531-535 (1995))

The Hb—NO spectrum has a distinct NIR feature at about 740 nm. If the mean optical pathlength through the tissue is measured at the same time, it is theoretically possible to quantify Hb—NO separately from those of Hb and $HbO_2$. However, it is more complicated to measure absolute concentrations of Hb—NO in tissue due to its strong scattering property. Therefore, the derivatives of the absorbance spectra are widely used in the multicomponent analysis to overcome the scattering problem.

Reflected NIR light in the range of 400-2500 nm, and particularly the spectrum from 700-1000 nm can be analyzed at successive sites along the vessel wall to determine the absorbance of Hb—NO, substantially as described by Ohdan et al. *Transplantation* 57:1674-1677 (1994), adapted for use with a fiber-optic catheter such as that described above. Alternatively, the characteristic NIR absorbance spectrum of nitrosyl tyrosine can be employed instead of nitrosyl hemoglobin. Areas demonstrating relatively higher levels of nitrosyl hemoglobin or nitrosyl tyrosine imply the presence of peroxynitrite or peroxynitrate, and in combination with other factors is suggestive of a vulnerable plaque.

As mentioned above, with respect to alternative sensing techniques for measuring plaque pH, oxidative stress and metabolites of nitric oxide may also be measured by chemiluminescence, ultraviolet fluorescence-induced and natural spectroscopy, and infrared reflectance spectroscopy. (See, for example, Crow, J. P. *Nitric Oxide* 1:145-57 (1997)). For invasive catheter-based multi-parameter detection, the NIR technique is preferred, however, for its widespread applicability to a multiplicity of chemical analytes.

Oxidized Collagen

As the most abundantly distributed and ubiquitous protein in the human body, the presence of collagen in tissues has important implications for the diagnosis of diseased states. The connective tissue matrix is considerably altered in a number of diseases and the nature of the alteration may depend upon the stage of the disease. For example, significant changes in connective tissue matrix and oxidative collagen are expected to be associated with aging, and the increased vulnerability of atherosclerotic plaque due to increased presence of oxygen species. Therefore, a multi-parameter examination of vessel may also include assessment of the oxidized collagen or connective tissue matrix content. NIRS is a very efficient way of monitoring connective tissue properties since the amide A-amide II combination band (~2.1 mm) can be easily measured in the NIR spectral region Lippman (*Exp Geron* 20:1-5 (1985).

Reflected NIR light at wavelengths characteristic for oxidized collagen is analyzed at successive sites along the vessel wall to determine the absorbance of amide bonds, substantially as described by Lippman (id) or Liu (*Biochim Biophys Acta* 1315:73-77 (1996)), modified for using the new NIR catheter described above. Areas along the vessel wall demonstrating greater amide bonding imply that greater levels of collagen oxidation are present.

Glucose, Lactate and Pyruvate

Glucose is the basic food supply for living cells. D-glucose occurs normally and in abundance both in blood and the interstitial fluid. In healthy individuals, regulatory mechanisms operate so that the blood glucose concentrations are generally maintained within the range of 45-130 mg/dL (2.5-7.2 mM) in a non-fasting individual. NIRS has been proposed as a means for measuring in vivo blood glucose value noninvasively for diabetic patients. The concept in that application is to allow NIR radiation to penetrate a vascular-equilibrated region of the body, followed by the acquisition of a spectrum of the tissue through either a transmission or reflectance measurement. Quantitative glucose information is then extracted from the measured spectrum through the use of suitable data processing methods. Lactate is measured similarly. In some embodiments of the present method, glucose and lactate levels in plaque and in normal vessel wall are measured by near-infrared spectroscopy by adapting the method taught by McShane et al. (*Appl Spectrosc* 52: 1073-1078 (1998) for use with the fiber optic catheter assembly described above.

A multi-parameter catheter diagnostic method as exemplified above employs the cumulative value of one or more of the tests for tissue low pH, hypoxia as indicated by oxyhemoglobin and oxidized cytochrome oxidase $aa_3$, oxidized cytochrome oxidase $aa_3$, oxidized collagen, lowered glucose level, elevated lactose level, presence of oxidant species as indicated by oxidized LDL and the NO metabolites nitrosyl hemoglobin and nitrosyl tyrosine, and other chemical parameters characteristic of inflamed plaque, to provide more comprehensive insight into the plaque inflammatory status than has before been possible. If desired, NIR detection of oxidized LDL fatty esters could also be included. By using the new multi-parameter catheter assembly, prediction of plaque rupture is accomplished with better accuracy and specificity than with previous methods, and having the additional advantage of requiring only a single invasive device. One preferred embodiment of the invention employs a catheter assembly capable of detecting areas where several or all of the following conditions exist: acidosis (low pH), NO, hypoxia (low $pO_2$), reactive oxygen species ($O_2^-$, OH, $H_2O_2$, for example, as oxidized low density lipoprotein cholesterol, and collagen), low glucose and high peroxynitrate and nitrosyl proteins. For other (non-cardiovascular) applications such as detection of infection, cancer, autoimmune reaction, wound or foreign body reaction it is not necessary to consider the NIR spectrum for oxidized LDL cholesterol, whose abundance in vulnerable plaque distinguishes it from other inflammatory reactions.

Detection of Plaque Cap Leakiness

Figure 14:
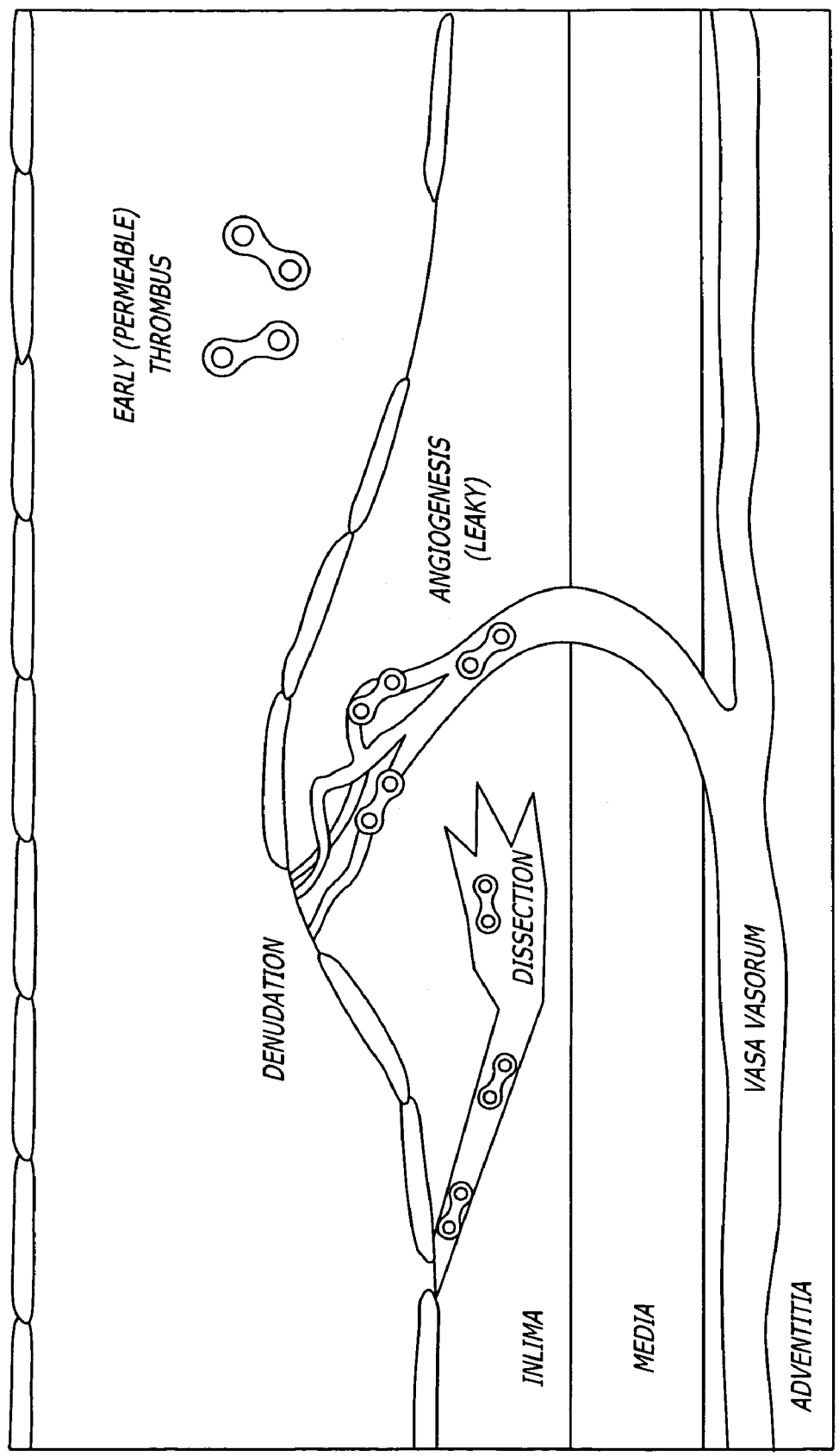
FIG. 14 is a conceptual drawing illustrating likely mechanisms of retention of contrast material in "leaky" atherosclerotic plaque.

In the course of developing the present invention, it was hypothesized by some of the inventors that progression of certain plaques that confer ≦50% diameter stenosis, i.e., the dangerous, more vulnerable plaques, could be predicted by fresh mural thrombus, plaque angiogenesis or cap leakiness. Studies were commenced to determine if these additional predictive factors are identifiable on an angiographic film as a "blush," or faint mural contrast remaining after passage of the angiographic contrast dye column. If, either due to disruption, unfolding of the plaque cap, or vasa vasorum delivery via intra-plaque hemorrhage, a fair amount of angiographic dye were to enter into a plaque during coronary angiography, such an occurrence and the resulting "blush" sign (retained contrast after the lumen has cleared) on an angiogram might be predictive for further progression of coronary heart disease, detectable by angiography. FIG. 14 is a conceptual illustration of likely mechanisms of dye retention in atherosclerotic plaque. Shown in cross-section are the intimal, medial and adventitial layers of the vessel, and the presence of epithelial cell denudation, early (permeable) thrombus, leaky angiogenesis, and dissection of the intimal layer.

The angiograms of hospital patients who because of angina (n=14) or myocardial infarction ("MI") (n=1) underwent two angiograms an average of 9.3 (±8.3 months) apart were examined. Two skilled reviewers in blind studies each analyzed 15 plaques that progressed (32±10% to 63±16% luminal narrowing), plus control lesions (proximal and distal) in a third vessel. The plaques were examined with respect to 14 points (identified in Table 1). It was determined that "blush" and "parent" location (just upstream of a branch) are strong predictors that a relatively low-stenotic lesion will progress to a thrombus or rupture, as shown by the data presented in Table 1.

TABLE 1

| Risk factors | Progressing Plaques n = 15 | Nonprogressing Plaques n = 32 | P Value |
| --- | --- | --- | --- |
| Plaque blush | 8 (53%) | 2 (6%) | .0008 |
| Calcium | 3 (20%) | 2 (6%) | .305 |
| Clot (mobile defect) | 2 (14%) | 0 | .097 |

TABLE 1-continued

| Risk factors | Progressing Plaques n = 15 | Nonprogressing Plaques n = 32 | P Value |
|---|---|---|---|
| TIMI-1 | 2 (14%) | 0 | .097 |
| TIMI-2 | 3 (20%) | 11 (34%) | .458 |
| Eccentric Lesion | 10 (66%) | 14 (44%) | .204 |
| Lesion length(mm) | 6.28 | 3.13 | .0007 |
| Irregularity | 2 (13%) | 2 (6%) | .583 |
| Haziness | 0 | 0 | N/A |
| Overhanging edges | 1 (6%) | 1 (3%) | 1.000 |
| Branch pt. Lesion | | | |
| Parent | 5 (33%) | 2 (6%) | .029 |
| Child | 3 (20%) | 1 (3%) | .541 |

Table 1 shows that plaque progression can often be predicted by anatomic location and particularly by residual dye "blush." TIMI-1 and TIMI-2 are conventional blood flow markers, wherein 0=no flow, 3=normal flow, and levels 1 and 2 are intermediate values. The sensitivity and specificity of plaque blush and branch point parent lesion were 54%, 94% and 33%, 94% respectively. The blush sign was significantly more common on the angiograms of those whose disease progressed afterward, leading to the conclusion that this mode of examination could be predictive of future coronary events. These clinical findings are supported by the pathology studies of others in which post mortem angiographic examination revealed that contrast media found its way into the core of plaque during angiography procedures, indicating that the plaque surface was ruptured nearby (Gronholdt, et al., id [see FIG. 1]; van Dantzig et al. *Eur Heart J* 7:987-91 (1986)).

Since the percent stenosis of a vessel indicated by angiographic examination typically correlates poorly with blood flow, identification of plaques that are already fissured or leaking is valuable for making interventional decisions concerning plaques of "intermediate" severity (i.e., inflamed but having an intact cap and/or not leaking) and for guiding medical therapy decisions. Fissuring and leakiness are features thought to increase the risk of thrombosis.

Figure 12:
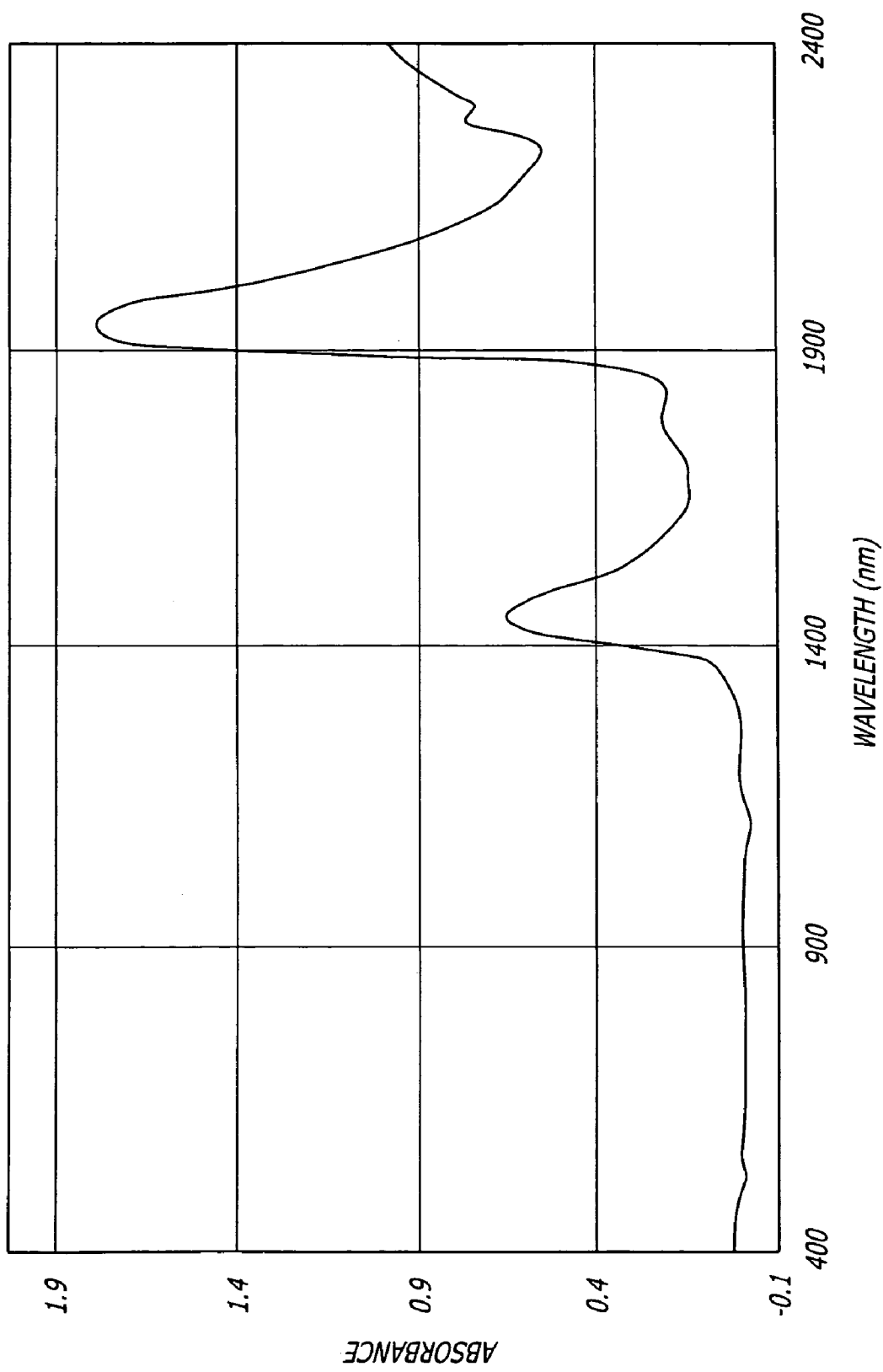
FIG. 12 is a graph showing the near-infrared spectral curve of the radiocontrast agent OMNIPAQUE® (iohexol)

By combining this plaque leakage detection method with the NIR detection of inflamed plaque histochemical constituents described above, another sensitive way of identifying the vulnerable plaques is possible which may be preferred in many clinical situations where angiography is performed. Accordingly, the above-described method of detecting vulnerable plaque is modified by first introducing into the vessel undergoing examination an angiography radiocontrast material, such as by intracoronary injection via the NIR catheter's perfusion lumen. Spectral data is then obtained for the spectrum characteristic of the angiographic contrast material, in addition to analysis for evidence of inflammation as described above. The angiogram is examined with respect to the points identified in Table 1 and the results are considered by the physician after studying the results obtained for each of the other parameters along the vessel wall. Plaques having significant multi-parameter indicators of inflammation and containing sequestered radiocontrast material would be considered to be the most dangerous ones and most in need of intervention, having progressed from the intermediate stage of vulnerability to high risk. FIG. 12 shows the near-infrared absorbance spectrum of OMNIPAQUE®, a conventional angiography radiocontrast dye. While the two largest absorbance peaks are attributed to water in the specimen, the dye molecule demonstrates sufficiently strong absorbance characteristics to permit in vivo detection in a plaque.

In an alternative method the radiocontrast material itself, or a biocompatible near-infrared indicator compound, is circulated in the target vessel for a sufficient time to permit uptake, or penetration, into the fissured or "leaky" plaques. Optionally, a suitable NIR indicator compound could also be mixed with the angiography medium. The presence or absence of the indicator compound in the interior of a plaque is detected by its characteristic NIR reflectance spectrum of the radiocontrast material or other indicator compound, while one or more of the inflammation indicating multi-parameters is being assessed along the vessel wall. Instead of a conventional angioscopy radiocontrast dye, another suitable NIR-absorbing material which can be taken up and sequestered by a leaky plaque or extravasation of vasa vasorum could be used, such as a biocompatible compound that has a distinctive NIR absorbance spectrum easily distinguishable from the spectra of other plaque-related analytes. For example, the hydroxyethyl starches HESPAN™ and PENTASPAN™ and dextran are detectable by NIR spectroscopy. These biocompatible starch-based macromolecules are being investigated for wide-spread use as a plasma replacement or extender during routine plasma exchange (Brecher et al. *J Clin Apheresis* 12:146-53 (1997); Rock et al. *J Clin Apheresis* 12:165-9 (1997)), and have also been employed in detecting pulmonary leakage in patients with acute lung injury and acute respiratory distress syndrome (J. Wang, personal communication (1998)). Another desirable contrast material would be one that has antioxidant properties, or one that neutralizes the acidity of vulnerable plaques. One radiocontrast or NIR indicator compound may be preferred over another for particular patients or in certain clinical situations for medical reasons, or in order to optimize conditions for distinguishing the spectral data of one parameter from another with the NIR catheter assembly of the invention.

Another alternative method of assessing plaque leakiness substitutes a magnetic resonance probe instead of employing near-infrared spectroscopy and the fiber optic catheter probe for an indicator compound inside of the vulnerable plaques. MR spectroscopy, or MR imaging, may be preferred in situations where non-invasive techniques are indicated instead of an intravascular fiber optic catheter. For this method the contrast material, or indicator material, is selected for its ability to provide a strong MR signal.

Still another option for detecting plaque leakiness is to substitute intravascular ultrasound for the near-infrared fiber optic spectroscopy assembly, in which case an injection of microbubbles (commercially available) is administered and ultrasound is used to detect microbubbles remaining inside the plaque after the column of microbubbles has cleared the vessel lumen.

Visible Imaging or Colorimetry in Conjunction with NIR Analysis of the Vessel Wall A significant number, if not all, vulnerable plaques are eroded or denuded of endothelial cells and are covered by a thin layer of clot, or mural thrombus. As mentioned previously in the background of the invention, it is generally thought that as an integral part of the natural history of atherosclerotic plaque, plaque rupture occurs relatively often. Not all plaque disruptions and their associated thrombi lead to an acute clinical event, however. An autopsy study of patients with coronary atheroma who died of sudden noncardiac causes revealed that 17% had had a small, recent plaque disruption with thrombus within the lipid core. (See, for example, Davies et al, *Eur Heart J* 10:203-8 (1989).) That study is supported by studies showing that subjects who die of a major plaque disruption have, on average, 2.5 smaller plaque events at other sites. (For example, see Falk E, *Circulation* 86:11130-42 (1992); and Falk E et al *Circulation* 92:657-71 (1995).)

These relatively smaller plaques are highly dangerous even though they did not result in complete occlusion at the first attack. Any significant change in hemodynamics, coagulability or vascular adhesion could lead to an acute clinical event with complete coronary occlusion. Therefore it is very important that the physician utilize the best means available for finding these vulnerable plaques and taking preventative action. Since these small, microthrombi-containing plaques seem to be characterized by red, brown or white mural thrombosis, a visible channel is also included in some of the preferred embodiments of the multi-parameter catheter for identifying microthrombi. Red clots (rich in fibrin and erythrocytes) are more frequently found on in areas of slow blood flow, while white clot (rich in platelets) typically initiates hemostasis and often precedes and triggers red clot formation. Brown-green clots contain bilirubin and hemosiderin and indicates that the clot is days to weeks old. Inclusion of calorimetric or visible image monitoring of the vessel wall during NIR exploration allows the user to improve the chances of identifying this kind of plaque. Such red, brown or white areas are also expected to show some differences in their NIR spectroscopic pattern as well. The inventors have determined (data not shown) that undisrupted inflamed vulnerable plaques, in contrast to what one expects of an ordinary inflammation site as seen elsewhere in the body, do not tend to be reddish. The inventors have found that vulnerable plaques are more of a yellow color, most likely due to the voluminous free fat content of these plaques (Casscells et al. *Lancet* 347: 1447-51 (1996) [see comments]; also reported by others such as Kleber *Eur Heart J* 19 Suppl C:C44-9 (1998); Thieme et al. *J Am Coll Cardiol* 28:1-6 (1996).) Measurement of fat content, however, is not a sufficient screening method because of the prevalence of yellow fatty streaks in the adult human blood vessel wall and because not all cholesterol contains the yellow pigment carotene. Lipid detection is also not as sensitive or specific an indicator of risky plaque as NIR spectroscopy of inflammation parameters or temperature heterogeneity of the plaques. Preferably, the more sensitive technique of colorimetry is employed instead of visual monitoring of the plaque wall to distinguish white clot from red clot on the vessel wall, since the very small thrombi in plaque are often not detectable by visual inspection. Colorimetry techniques are well known and are readily adaptable for use in the visible wavelength range of the multi-parameter analysis assembly of the invention to detect very small red, white or brown colored sites along a vessel wall.

Temperature Heterogeneity

An important physical attribute of inflammation in a site of infection, cancer, a wound, in auto-immune disease, or in an inflamed atherosclerotic plaque which may be advantageously considered with the other indicators described above is elevated temperature. In the case of detection of vulnerable atherosclerotic plaque, in situations where the relative temperature of the site can also be determined, a temperature difference of about 1.5°-2° C. above vessel ambient temperature strongly suggests the presence of active inflammation in a plaque. Preferably temperature measurements are conducted prior to NIR examination of the vessel, to avoid artifactual warming, and is performed by a non-invasive method such as magnetic resonance imaging, as discussed elsewhere in more detail.

Evaluation of a Candidate Anti-Atherosclerotic Therapy

The multi-parameter detection methods and apparatus exemplified above is also expected to be advantageous for use in experimental animal models to detect changes in the level of risk of particular plaques. The effectiveness of a given anti-atherosclerotic therapy can be evaluated after cholesterol feeding and after arterial injury simulating a human angioplasty procedure. The animal is first examined by establishing the level of risk of particular plaques in a vessel, as described above. The desired treatment is administered for a given period of time, and the status of two or more parameters are again monitored along the same vessel wall. Optionally, the anatomo-physiological features of the vessel wall are also monitored and correlated with the inflamed plaque parameters to provide even more information about particular sites.

The new multi-parameter detection method and catheter assembly is also expected to find extensive use initially as a tool for the development of more precise calibration standards for subsequent in vivo applications. The inventors' continuing investigations include developing an in vivo animal model of plaque rupture, based on what we have learned from ex vivo pathology and physiopathology of vulnerable plaque.

Therapeutic Treatment of a Vulnerable Atherosclerotic Plaque

If it is determined by a detection method exemplified above that a particular atherosclerotic plaque is sufficiently vulnerable to merit intervention, an appropriate treatment is implemented in the patient, targeting the sites so identified. Such treatment will preferably include gentle heat treatment as disclosed in co-pending U.S. patent application Ser. No. 08/934,260 (the disclosure of which is incorporated herein by reference to the extent that it provides pertinent methods and materials not specifically set forth herein), if medically appropriate for a particular patient. In order to down-regulate macrophage activity and/or to induce macrophage apoptosis, appropriate gentle heating of the vulnerable plaques can be accomplished with any suitable heating catheter that is able to regulate the temperature applied to the plaque at 39°-44° C. for 5 to 60 minutes, and which includes means for perfusing the downstream portion of the vessel.

Alternatively, a suitable localized treatment regimen may include balloon angioplasty, laser angioplasty, heated balloon (RF, ultrasound or laser) angioplasty, surgical atherectomy, laser atherectomy, the placement of an appropriate stent, or another conventional mechanical or irradiation treatment method. A suitable pharmacological treatment regimen may also be applied locally to an at-risk plaque, at the option of the physician. Such treatments include anti-coagulants, fibrinolytic, thrombolytic, anti-inflammatory, anti-proliferative, immunosuppressant, collagen-inhibiting, endothelial cell growth-promoting, and other conventional pharmacologically appropriate local treatments effective for reducing or eliminating inflamed plaque.

All patents and publications referred to in this application are incorporated herein by reference to the same extent as if each was specifically indicated as being incorporated by reference and to the extent that each provides pertinent methods and materials not specifically set forth herein.

While the preferred embodiment of the invention has been shown and described, modifications thereof can be made by one skilled in the art without departing from the spirit and teachings of the invention. For instance, the catheter based methods exemplified above could be modified to provide a non-invasive way of identifying vulnerable plaque. In this case, the fiber optic catheter is omitted and the desired chemical and physical parameters are evaluated non-invasively by magnetic resonance (MR) diffusion imaging, MR spectroscopy, near-infrared spectroscopy and scintigraphy (See, for example, Refs. 70-80 in Gronholdt, id.). The embodiments described herein are exemplary only, and are not limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

What is claimed is:

1. A method of simultaneously measuring in a living vessel at least two chemical parameters associated with inflamed vulnerable atherosclerotic plaque, the method comprising:
    providing a fiber optic catheter having an illumination fiber bundle and a detection fiber bundle capable of, respectively, directing radiation onto or receiving radiation from a site on a vessel wall, said catheter having means for reducing optical interference by blood or other fluid within a vessel when undergoing examination;
    providing a source of 400-2500 nm wavelength radiation operatively linked to said illumination fiber bundle;
    providing a spectrometer operatively linked to the detection fiber bundle;
    providing a processor operatively linked to said spectrometer containing algorithms and reference measurements for at least two chemical parameters associated with inflamed vulnerable atherosclerotic plaque, said spectrometer and processor together being capable of receiving and analyzing spectral data collected by said detection fiber bundle and reporting corresponding parameter measurements;
    providing a display system capable of receiving and displaying a report from said processor;
    measuring a first parameter at a multiplicity of sites on the vessel wall;
    measuring at least one other parameter at said multiplicity of sites on a vessel wall;
    analyzing a multiplicity of parameter measurements corresponding to said multiplicity of sites so that a qualitative or quantitative value for each said parameter is obtained; and
    performing a determination regarding inflamed vulnerable atherosclerotic plaque at said multiplicity of sites based on the qualitative or quantitative value for each said parameter, wherein the results of said determination are reported on said display system, and wherein said first parameter is chosen from the group consisting of pH, oxyhemoglobin, deoxyhemoglobin, cytochrome oxidase $aa_3$, reduced cytochrome oxidase $aa_3$, nitrosyl hemoglobin, nitrosyl tyrosine, glucose, lactate, and oxidized collagen, and wherein said at least one other parameter is chosen from the group consisting of pH, oxyhemoglobin, deoxyhemoglobin, cytochrome oxidase $aa_3$, reduced cytochrome oxidase $aa_3$, nitrosyl hemoglobin, nitrosyl tyrosine, glucose, lactate, oxidized LDL cholesterol, and oxidized collagen.

2. The method of claim 1 wherein said first parameter is pH.

3. The method of claim 1 wherein said first parameter is oxyhemoglobin and said at least one other parameter comprises deoxyhemoglobin.

4. The method of claim 1 wherein said first parameter is cytochrome oxidase $aa_3$ and said at least one other parameter comprises reduced cytochrome oxidase $aa_3$.

5. The method of claim 1 wherein said first parameter is nitrosyl-hemoglobin or nitrosyl-tyrosine.

6. The method of claim 1 wherein said first parameter is oxidized collagen.

7. The method of claim 1 wherein said first parameter is glucose.

8. The method of claim 1 wherein said first parameter is pH, and said at least one other parameter includes oxidized collagen and a parameter chosen from the group consisting of oxyhemoglobin, deoxyhemoglobin, cytochrome oxidase $aa_3$, reduced cytochrome oxidase $aa_3$, nitrosyl hemoglobin, nitrosyl tyrosine, glucose, andlactate, and oxidized LDL cholesterol.

9. The method of claim 1 wherein said step of providing a processor includes:
    providing a processor operatively linked to said spectrometer, said processor containing algorithms and reference measurements for at least two chemical parameters associated with inflamed vulnerable atherosclerotic plaque, and containing algorithms and reference measurements for colorimetric measurement of thrombi colored red, brown, greenish-brown and white, said spectrometer and processor together being capable of receiving and analyzing spectral data collected by said detection fiber bundle and reporting corresponding parameter and colorimetric measurements.

10. The method of claim 1 wherein providing said display system capable of receiving and displaying a report from said processor includes providing a monitor capable of displaying a color image of said vessel wall.

11. The method of claim 1 further comprising detecting an indicator dye associated with a plaque whereby a plaque cap fissure is revealed.

12. The method of claim 11 wherein said step of detecting an indicator dye comprises detecting a radiocontrast dye associated with a plaque by intraplaque leakage.

13. The method of claim 11 wherein said step of detecting an indicator dye comprises detecting a biocompatible molecule having a distinct NIR absorbance spectrum.

14. The method of claim 13 wherein said step of detecting an indicator dye comprises detecting a hydroxyethyl starch.

15. A method of detecting in a living vessel an atherosclerotic plaque at risk of rupturing or thrombosing, the method comprising:
    qualitatively or quantitatively measuring at least two parameters associated with inflamed vulnerable plaque in accordance with the method of claim 1;
    measuring dye sequestered beneath the surface of a site along a vessel wall; and
    analyzing said dye measurement together with said parameter measurements to distinguish inflamed vulnerable plaque from relatively stable plaque and normal vessel wall and to determine predictive level of risk of rupture or thrombosis for at least one site or group of sites on a wall of said vessel.

16. The method of claim 15 wherein said measuring of dye sequestration is performed with said fiber optic catheter, said dye containing a 400-2,500 nm wavelength radiation absorbing chromophore, and said processor additionally containing algorithms and reference measurements for analysing reflected or scattered radiation from said chromophore.

17. The method of claim 15 wherein said measuring of dye sequestration is performed by angiography, said dye is radiopaque, and said signal processor is also capable of receiving and analyzing said angiographic measurement.

18. A method of detecting a vulnerable atherosclerotic plaque on a vessel wall comprising the method of claim 15 and additionally
monitoring the visible color image of said site; and
analyzing said visual image together with said parameter and dye penetration measurements.

19. A method of treating a patient known to be suffering from atherosclerotic vessel disease and suspected of being at risk of experiencing a plaque rupture and/or an occlusive thrombotic event, the method comprising:
detecting an atherosclerotic plaque at risk of rupturing or thrombosing according to the method of claim 15, said method including monitoring the visible color image of said site and analyzing said visual image together with said parameter and dye measurements;
determining from said predicted level of risk for at least one site or group of sites on a wall of said vessel at least one vulnerable plaque for targeting treatment;
applying a local treatment to at least one so-determined target plaque, said treatment chosen from the group consisting of balloon angioplasty, laser angioplasty, heated balloon (RF, ultrasound or laser) angioplasty, surgical atherectomy, laser atherectomy, the placement of an appropriate stent, another conventional mechanical or irradiation treatment method, and pharmacological treatment regimens including anticoagulants, fibrinolytic, thrombolytic, anti-inflammatory, anti-proliferative, immunosuppressant, collagen-inhibiting, endothelial cell growth-promoting, and other conventional pharmacologically appropriate local treatments effective for reducing or eliminating inflamed plaque.

20. A method of distinguishing vulnerable plaque in need of therapeutic intervention from relatively stable plaque or non diseased tissue in a living vessel wall comprising the method of claim 1 wherein performing a determination includes comparing said qualitative or quantitative values for a site or group of adjacent sites to similarly obtained values for another site or group of sites along the vessel wall, so that a qualitative or quantitative value for each said parameter is reported by the display system for a particular site or region on a vessel wall expressed in terms relative to other sites or groups of sites along the same vessel wall.

21. A method of detecting an inflamed vulnerable atherosclerotic plaque on a vessel wall comprising:
providing a device comprising a spectrometer operatively linked to a fiber optic catheter and a processor, wherein the spectrometer and processor together are configured to receive and analyze spectral data collected by said fiber optic catheter and report corresponding parameter measurements;
operating said device to identify areas on said vessel wall having pH<7.2;
operating said device to identify areas on said vessel wall having an amount of oxidized collagen indicative of a thin or weak plaque cap;
operating said device to identify areas on said vessel wall having red microthrombi;
operating said device to identify areas on said vessel wall that have taken up and sequestered an indicator dye beneath the surface of a vessel;
correlating at least two of said identified areas with a site or group of sites on said vessel wall; and
calculating a predictive level of risk of plaque rupture for each said site or group of sites.

22. An improved method of detecting vulnerable atherosclerotic plaque in vivo in which a chemical or biochemical component of a plaque is measured using a device comprising a fiber optic catheter operatively linked to a spectrometer, the improvement comprising measuring at least two different analytes associated with activated macrophages, said analytes chosen from the group consisting of pH, oxyhemoglobin, deoxyhemoglobin, nitrosyl hemoglobin, nitrosyl tyrosine, oxidized cytochrome $aa_3$, reduced cytochrome $aa_3$, glucose, lactate, oxidized LDL cholesterol and oxidized collagen; and
detecting inflamed vulnerable atherosclerotic plaque at a multiplicity of sites based on a qualitative or quantitative value for each said measured analyte at said sites.

23. The method of claim 22 wherein said method includes using visible or near-infrared spectroscopy to measure said analytes.

24. The method of claim 22 wherein said method includes using magnetic resonance spectroscopy to measure said analytes.

25. An improved method of differentiating atherosclerotic plaque at risk of rupturing and occluding from plaque not presently at risk in which optical radiation from a site along a vessel wall is analyzed using a device comprising a fiber optic catheter operatively linked to a spectrometer, the improvement comprising identifying a site on said vessel wall by analyzing for indicia of actively metabolizing cells, wherein said indicia include a first parameter selected from the group consisting of pH, oxyhemoglobin, deoxyhemoglobin, cytochrome oxidase $aa_3$, reduced cytochrome oxidase $aa_3$, nitrosyl hemoglobin, nitrosyl tyrosine, glucose, lactate, and oxidized collagen, and at least a second parameter selected from the group consisting of pH, oxyhemoglobin, deoxyhemoglobin, cytochrome oxidase $aa_3$, reduced cytochrome oxidase $aa_3$, nitrosyl hemoglobin, nitrosyl tyrosine, glucose, lactate, oxidized LDL cholesterol, and oxidized collagen.

26. A method of detecting infection, cancer, wound or autoimmune disease comprising;
providing a device comprising a spectrometer operatively linked to a fiber optic catheter and a processor, wherein the spectrometer and processor together are configured to receive and analyze spectral data collected by said fiber optic catheter and report corresponding parameter measurements;
detecting with said device inflammation associated with said infection, cancer, wound or autoimmune disease, said detecting comprising measuring at a site in the body at least two different parameters chosen from the group consisting of pH, oxyhemoglobin, deoxyhemoglobin, cytochrome oxidase $aa_3$, reduced cytochrome oxidase $aa_3$, nitrosyl hemoglobin, nitrosyl tyrosine, glucose and lactate and performing a determination regarding infection, cancer, wound or autoimmune disease at said site based on a qualitative or quantitative value for each said measured parameter at said site.

27. A system for diagnosing an atherosclerotic plaque at risk of rupture or thrombosis, comprising:
a catheter having a proximal end and a distal end and having an illumination lumen and a detection lumen therein;
one or more optical illumination fibers within said illumination lumen, said optical illumination fibers capable of transmitting approximately 400 to 2500 nm wavelength radiation;

one or more optical detection fibers within said detection lumen, said optical detection fibers capable of transmitting approximately 400 to 2500 nm wavelength radiation;

a light source operatively linked to the proximal end of said catheter, said light source capable of emitting approximately 400 to 2500 nm wavelength radiation;

a spectrometer operatively linked to said one or more optical detection fibers;

a processor operatively linked to said spectrometer and containing algorithms and reference data for determining values for at least two different parameters associated with actively metabolizing cells of inflamed atherosclerotic plaque, wherein said at least two different parameters are selected from the group consisting of oxyhemoglobin, reduced hemoglobin, oxidized cytochrome oxidase $aa_3$, nitrosyl hemoglobin, nitrosyl tyrosine, pH, glucose, lactate, oxidized LDL cholesterol, and oxidized collagen, and for performing a determination regarding atherosclerotic plaque at risk of rupture or thrombosis based on the values for each said parameter.

28. A method of differentiating atherosclerotic plaque at risk of rupturing, comprising:

identifying sites containing indicia of highly metabolically active cells using the system of claim 27; and differentiating the vulnerable atherosclerotic plaque based upon the location of said highly metabolically active cells.

29. A method of detecting vulnerable atherosclerotic plaque, comprising:

measuring analytes comprising a chemical or biochemical component of plaque with a device comprising a spectrometer operatively linked to a fiber optic catheter and a processor, wherein the spectrometer and processor together are configured to receive and analyze spectral data collected by said fiber optic catheter and report corresponding chemical or biochemical component measurements, wherein said analytes are associated with activated macrophages; and identifying the vulnerable atherosclerotic plaque based upon the location and measurements of said analytes, wherein said analytes comprise a first analyte selected from the group consisting of pH, oxyhemoglobin, deoxyhemoglobin, cytochrome oxidase $aa_3$, reduced cytochrome oxidase $aa_3$, nitrosyl hemoglobin, nitrosyl tyrosine, glucose, lactate, and oxidized collagen, and at least a second analyte selected from the group consisting of pH, oxyhemoglobin, deoxyhemoglobin, cytochrome oxidase $aa_3$, reduced cytochrome oxidase $aa_3$, nitrosyl hemoglobin, nitrosyl tyrosine, glucose, lactate, oxidized LDL cholesterol, and oxidized collagen.

30. The method of claim 29 further comprising measuring said analytes by using visible and near-infrared spectroscopy.

* * * * *

UNITED STATES PATENT AND TRADEMARK OFFICE
CERTIFICATE OF CORRECTION

PATENT NO. : 7,603,166 B2 Page 1 of 1
APPLICATION NO. : 10/640570
DATED : October 13, 2009
INVENTOR(S) : Casscells, III et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1796 days.

Signed and Sealed this

Fifth Day of October, 2010

David J. Kappos
*Director of the United States Patent and Trademark Office*